(12) United States Patent
Holmgren et al.

(10) Patent No.: US 6,908,898 B1
(45) Date of Patent: Jun. 21, 2005

(54) ANGIOGENESIS RELATED MOLECULES

(75) Inventors: Lars Holmgren, Tomtebogstan 26, SE-113 38, Stockholm (SE); Boris Troyanovsky, Rinkebysvangen 91, Apartment 202, SE-103 74, Spanga (SE)

(73) Assignees: Lars Holmgren, Stockholm (SE); Boris Troyanovsky, Spanga (SE)

( * ) Notice: Subject to any disclaimer, the term of this patent is extended or adjusted under 35 U.S.C. 154(b) by 0 days.

(21) Appl. No.: 09/332,063

(22) Filed: Jun. 14, 1999

Related U.S. Application Data

(60) Provisional application No. 60/089,266, filed on Jun. 15, 1998, and provisional application No. 60/114,386, filed on Dec. 29, 1998.

(51) Int. Cl.$^7$ ...................... A61K 38/00; C07K 14/705
(52) U.S. Cl. ............................ 514/12; 514/21; 530/350
(58) Field of Search ..................... 514/12, 21; 530/350, 530/380, 381, 382, 300, 328; 536/23.1

(56) References Cited

U.S. PATENT DOCUMENTS 5,679,350 A  * 10/1997  Jankun et al.
5,916,572 A  *  6/1999  Reed et al.

FOREIGN PATENT DOCUMENTS

EP          0206400 A1    12/1986

OTHER PUBLICATIONS

Troyanovsky et al (Journal of Cell Biology, 2001, vol. 152, pp. 1247–1254).*
Amino acid database (U.S. Patent 5,916,572), 1995.*
Bork, Peer. Powers and Pitfalls in Sequence Analysis: The 70% Hurdle. Genome Research 10:398–4000, 2000.*
Petersen, T. et al. Characterization of the Gene for Human Plasminogen, a Key Proenzyme in the Fibrinolytic System. Journal of Bio. Chem. 205(11):6104–6111, 1990.*
Amino acid database, Accession #O13028, 1997.*
Amino acid database, Accession #W00024, 1997.*
Schartz et al. A superactive insulin: [B10–Aspatic acid] Insulin (human). Proc. Natl. Acad. Sci. 84:6408–6411, 1987.*
Lin et al. Structure–Function Relationships in Glucagon: Properties of Highly Purified Des–His(1)–, Monoiodo–, [Des–Asn (28), Thr (29)] (homoserine Lactone (27)–glucagon. Biochemistry 14(8): 1559–1563, 1975.
Biotechnology Industry Organization, Critical Synergy: The Biotechnology Industry and Intellectual Property Protection, 1994.
Claesson–Welsh et al., Proc. Natl. Acad. Sci. USA, Vo., 95, May 1998, pp. 5579–5583.
O'Reilly et al., Nature Medicine, vol., 2, No. 6, Jun. 1996, pp. 689–692.
Wilson et al., Nature, vol. 368, Mar. 3, 1994, pp. 32–38.
Moser, Tammy L. et al. *Proc. Natl. Acad. Sci. USA*, vol. 96, No. 6, pp. 2811–2816, Mar. 16, 1999.
Claesson–Welsh, Lena, *Proc. natl. Acad. Sci. USA*, vol. 95, No. 10, pp. 5579–5583, May 12, 1998.
Kost, Christine et al. *Eur. J. Biochem*, vol. 236, No. 2, pp. 682–688, Mar. 1, 1996.
Database EMSTS Accession No. G16015, Jan. 25, 1996, Murray M. et al. XP002121366.

* cited by examiner

*Primary Examiner*—Karen A. Canella
(74) *Attorney, Agent, or Firm*—Kenyon & Kenyon

(57) ABSTRACT

The present invention provides the sequence of a protein capable of acting as an angiostatin receptor as well as the nucleic acid sequence thereof. The invention also relates to the use thereof in screening methods, wherein novel substances are created exhibiting the same advantageous antiangiogenic properties as angiostatin.

15 Claims, 12 Drawing Sheets

Fig._1

-His, +3-AT

Fig. 4

| Angiostatin | Plasminogen |
|---|---|
| Big-3 RO | Big-3 RO |

ID

ANGIOGENESIS RELATED MOLECULES

This application claims priority on provisional Application Nos. 60/089,266 and 60/114,386 filed on Jun. 15, 1998 and Dec. 29, 1998, the entire contents of which are hereby incorporated by reference.

TECHNICAL FIELD

The present invention relates to the field of angiogenesis, and more specifically to novel molecules, such as proteins and peptides, whereby novel anti-angiogenic substances may be developed. The invention also relates to methods for developing such substances.

BACKGROUND

Almost all of the tissue of a mammalian body comprises a fine mesh of very thin blood vessels, each of which is thinner than a human hair. Usually, neither the number nor the size of these vessels increase, since the division of the endothelial cells covering the vessels is slow, actually up to several years. The exceptions are for example during wound healing and menstruation, when the vessels grow rapidly. However, that is during a limited period of time and the cell division ceases thereafter.

The generation of new blood vessels from existing ones is called angiogenesis. Angiogenesis has been associated to cancer and the formation of tumors as well as to other conditions, such as diabetes retinopathy, rheumatoid arthritis and even some inflammatory conditions. Accordingly, a considerable research effort is made world-wide to find ways of preventing and inhibiting the angiogenic process. If this were possible, tumor growth could be controlled and useful therapies could be developed regarding the above mentioned conditions.

There exists numerous pieces of evidence showing that tumors are depending on de novo formation of blood vessels for expansion beyond a mass of a few $mm^3$. The angiogenesis is triggered by factors secreted by the tumor cells. It has recently been discovered that tumors through unleashed proteolytic activity generates peptide fragments, which show anti-angiogenic activities. One example is the molecule angiostatin, which is a fragment of plasminogen.

Plasminogen is a substance in blood plasma which, when activated, forms plasmin or fibrinolysin, an enzyme involved in the coagulation of blood. Plasminogen itself lacks any detectable anti-angiogenic activity. It has been found (Judah Folkman et al, Harvard Medical School, Boston) that a part of this endogenous protein, more specifically the first four kringle domains, is capable of preventing the endothelial cells from dividing. This part of plasminogen has been denoted angiostatin, and a great deal of research within this field is centred around this molecule. The prior art has shows that angiostatin inhibits endothelial cells specifically in vitro and blocks angiogenesis in vivo. Systemic treatments with subcutaneous injections of angiostatin induces in vivo dormancy in a wide range of tumors in SCID mice (O'Reilly et al., Nature Med., vol. 2, p. 689, 1996). No detectable toxicity has been detected in these animals even after months of treatment. Angiostatin shows two levels of specificity: it induces apoptosis specifically in endothelial cells in vitro (Claesson-Welsh et al., Proc. Natl. Acad. Sci., USA, vol. 95, p. 5579, 1998) and only affects endothelial cells active in angiogenesis in vivo. It has not shown to negatively affect cells in established vessels.

Angiostatin does indeed exhibit some advantageous properties, inter alia as it is an endogenous substance. However, the disadvantages associated with its possible use for medical purposes cannot be neglected. One is that the half life thereof is very short, it may be counted in hours, thereby requiring a frequent administration thereof. This far, the efficiency thereof has proven to be rather low, which fact necessitates the use of large doses thereof. These two disadvantages are in themselves strong motives for directing further research towards the finding of alternative, smaller and/or more efficient molecules to be used as medicaments.

SUMMARY OF THE INVENTION

The present invention solves the problems associated with angiostatin as defined above by providing a human protein, which has been named "ABP-1", defined by its ability to bind a fragment of plasminogen, preferably the first four Kringle domains (K1–K4) thereof, the said fragment being characterized by anti-angiogenic biological activity.

ABP-1 comprises an amino acid sequence substantially similar to that shown in SEQ ID NO. 2. Variants and fragments of ABP-1 are encompassed in the present invention.

Also encompassed in the present invention are the homologs of ABP-1 in other species, especially in other mammals.

In a further aspect, the invention provides isolated nucleic acid molecules comprising a sequence that codes for ABP-1 or for a polypeptide substantially similar to ABP-1, including its variants, fragments and homologs.

It is another object of the present invention to provide nucleic acid probes whose sequence is derived from SEQ ID NO.1; these probes may be used as research tools as well as in diagnostic methods, for example to detect and measure ABP-1 biosynthesis in tissues and cells.

Accordingly, it is an object of the present invention to provide a diagnostic method for detecting the presence and the amount of ABP-1 or its variants and fragments in tissues and cells.

The present invention also includes screening methods for identifying a compound capable of interacting with ABP-1 or its variants and fragments. The screening method can be in any configuration well known to those skilled in the art.

It is a further object of the present invention to provide compounds identified with the said screening method and capable of modulating the biological activity of ABP-1 or its variants and fragments.

It is a further object of the present invention to provide a pharmaceutical composition comprising as active ingredient the compound identified with the above screening method.

It is still a further object of the present invention to provide antibodies directed against epitopes present in ABP-1 or its variants and fragments as well as cell producing the antibody.

It is a further object of the present invention to provide a vector comprising the nucleotide sequence of ABP-1 or its variants and fragments.

It is a further object of the present invention to provide a cell containing the above vector.

Definitions

In the present application, the following terms are used in the meanings defined below.

As used herein, the term "angiogenesis" relates to the generation of new blood vessels into a tissue or organ. As mentioned above, under normal physiological conditions, humans and animals undergo angiogenesis only in very specific restricted situations. For example, angiogenesis is normally observed in wound healing, fetal and embryonal development and formation of the corpus luteum and placenta.

The term "endothelium" relates to the thin layer of flat epithelial cells, that lines serous cavities, lymph vessels and blood vessels, The term "endothelial inhibiting activity" relates to the capability of inhibiting the growth of endothelial capillary endothelial cells.

The term "an angiogenesis associated protein" relates to a protein capable of interacting in the angiogenesis, such as a receptor binding an anti-angiogenic substance.

The term "substantially similar", when used in reference to the amino acid sequence of SEQ ID NO.2, SEQ ID NO.3 and SEQ ID NO.4, means an amino acid sequence having an high degree of sequence homology to SEQ ID NO.2, SEQ ID NO.3 and SEQ ID NO.4. A high degree of homology means at least approximately 80% amino acid homology, preferably at least approximately 90% amino acid homology, more preferably at least approximately 95% amino acid homology and most preferably at least approximately 98% amino acid homology.

The term "specifically hybridizing to" refers to the binding, duplexing or hybridizing of a molecule only to a particular nucleotide sequence under stringent conditions when the sequence is present in a complex mixture (e.g. total cellular) of DNA or RNA. The term "stringent conditions" relates to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na ion, typically about 0.01 to 1.0 M Na ion (or other salts) at pH 7.0 to 8.3 and the temperature is at least about 30° C. for short probes (e.g. 10 to 50 nucleotides) and at least about 60° C. for longer probes. Stringent conditions may also be achieved with the addition of destabilizing agents, such as formamide.

BRIEF DESCRIPTION OF THE DRAWINGS

FIG. 4 compares the binding of recombinant "Big-3" to angiostatin and plasminogen, respectively.

DETAILED DESCRIPTION OF THE INVENTION

Figure 1:
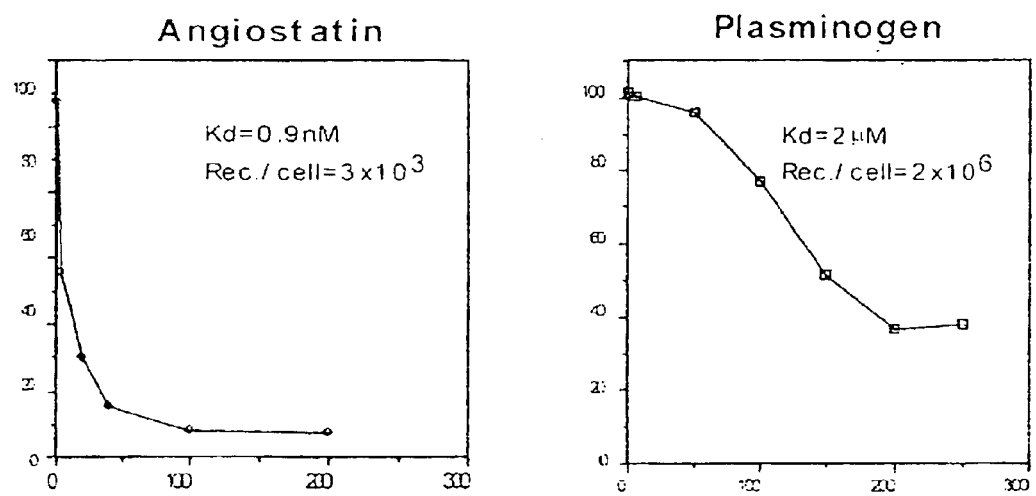
FIG. 1 shows the binding of $^{125}$I-labelled angiostatin and plasminogen to bovine microcapillary endothelial cells in vitro, Units in abscissa represent the fold molar excess of cold angiostatin and plasminogen, respectively.

The present invention relates to an isolated human angiogenesis-associated protein capable of binding a fragment of plasminogen, preferably an N-terminal fragment, such as kringle domains 1 to 4 and/or kringle 5. Thus, the protein of the invention acts as a receptor of plasminogen fragments, in particular as a receptor of angiostatin and/or kringle 5 domain of plasminogen. The protein of the invention can be synthesized by biological or chemical methods (e.g. recombinant gene expression and peptide synthesis). Recombinant techniques include gene cloning or amplification by in vitro methods, such as the polymerase chain reaction (PCR), the ligase chain reaction (LCR), the transcription-based amplification system (TAS) or the self-sustained sequence replication system (SSR). A wide variety of cloning and in vitro amplification methodologies are well-known to those skilled in the art. Examples of these techniques are e.g. found in Berger and Kimmel, *Guide to Molecular Cloning Techniques,* Methods in Enzymology 152 Academic Press, Inc., San Diego, Calif. (Berger). The present invention includes proteins which comprise amino acid sequences substantially similar to those shown in SEQ ID NO.2, SEQ ID NO.3 and SEQ ID NO.4. A comparison of the protein sequence of SEQ ID NO. 2 with the sequences present in all available data bases showed a homology of 23.7% with a hypotetical protein of *Caenorhabditis elegans* encoded by a putative open reading frame located in the central cluster of chromosome III of this organism (described in R. Wilson et al., Nature, vol. 368, 3 Mar. 1994, p. 32–38). No function has been attributed to this hypotetical protein.

According to the definition given above, it is to be understood that all polypeptides capable of binding a fragment of plasminogen and having an amino acid sequence which has at least approximately 80% sequence homology, preferably approximately 90% sequence homology, more preferably approximately 95% sequence homology and most preferably approximately 98% sequence homology to SEQ ID Nos.2, 3 or 4, are contemplated as being included in the present invention. These variant forms may result. e.g., from alternative splicing or differential expression in different tissue of the same source organism. The variant forms may be characterized by, e.g., amino acid insertion, deletion or substitution. A preferred variant form of ABP-1 is illustrated in SEQ ID NO. 3 (see below).

A particularly preferred embodiment of the present invention is a fragment of ABP-1 named Big-3 which will be described in greater details below and which includes the angiostatin-binding domain of ABP-1 (SEQ ID NO. 4).

In a further embodiment, the present invention provides peptides which comprises at least about 5, preferably at least about 10 contiguous amino acid residues of SEQ ID NO 2 or any variant or fragment thereof. However, the most advantageous size of the peptide will be depending on the intended future use thereof and the present invention is not limited to the above stated number of amino acids residues.

Also included in the present invention are homologs of ABP-1 and Big-3 in other species, in particular in other mammals. The term "homolog" refers to proteins exerting substantially the same biological function of the proteins of the invention, regardless of the homology existing between the corresponding amino acid sequences.

In another aspect, the present invention relates to isolated nucleic acid molecules comprising a sequence that codes for the proteins and peptides of the invention, including the variants, fragments and homologs as defined above. In a preferred embodiment, the nucleic acid molecule has the sequence of SEQ ID NO. 1. This sequence presents a 5 (from nucleotide 1 to nucleotide 796) and a 3' (from nucleotide 2825 to nucleotide 6463) untranslated regions. In another preferred embodiment the nucleic acid molecule has the sequence from nucleotide 797 to nucleotide 2824 of SEQ ID NO. 1. In another preferred embodiment the nucleic acid sequence encodes the ABP-1 fragment named Big-3 (illustrated in SEQ ID NO. 4) and it comprises the nucleotide sequence from position 2180 to position 2608 of SEQ ID NO. 1. All the nucleotide sequences encoding the polypeptides of the invention and differing from the nucleotide sequence of SEQ ID NO. 1 or fragment thereof by way of the degeneracy of the genetic code, are considered part of the invention. Sequencing analysis has revealed the presence of a possible polymorfism in the codon 1199–1201 of SEQ ID NO. 1, wherein a codon for Asn, Ser or Asp maybe present; a further region corresponding to nucleotide positions 1238 to 1246 of SEQ ID NO.1 has been found to code for the tripeptide Glu-Leu-Ala or for the tripeptide Thr-Trp-Pro. These variations in the amino acid sequence of ABP-1 are illustrated in SEQ ID NO. 3 which constitutes another preferred protein of the invention. Also included in the present invention are nucleotide molecules encoding a homolog of ABP-1 or fragment thereof.

The present invention further comprises a nucleic acid capable of specifically hybridizing, under stringent conditions, to any one of the nucleic acid molecules of the invention described above.

Where the nucleic acids according to the invention are to be used as probes, it is often desirable to label the sequences with detectable markers. Such markers may include any composition detectable by spectroscopic, photochemical, biochemical, immunochemical, electrical, optical or chemical means. The markers may be incorporated by any of a number of means well known to those of skill in the art. Methods for detecting such markers are also well known in the art and disclosed in the literature. The probes find a useful application in diagnostic application, for example to detect and measure ABP-1 biosynthesis in tissues and cells.

In another aspect, the present invention provide screening methods or assays, wherein molecules that exhibit the same properties as angiostatin and/or kringle 5 are screened for. In a typical screening method a compound capable of activating the angiostatin signal transduction pathway is identified through a high throughput cell-based screen. Such screen rely on a reporter gene driven by an angiostatin responsive element that is stably transfected into an angiostatin-responsive cell line. The responsive element is linked to a reporter gene, e.g. the gene for luciferase; upon binding of the compound to the protein of the invention, the intracellular pathway is activated thus causing an increase in the reporter gene activity that can be detected.

The compounds identified through the screening method hereby described are within the scope of the present invention. Such compounds are preferably low molecular weight molecules of peptidic or non-peptidic nature. Thanks to their small size they are more practical for use for medicinal purposes, compared to angiostatin. These molecules and the uses thereof are described in more detail below.

The proteins and peptides according to the invention may be synthesized using standard chemical peptide synthesis techniques. For solid phase synthesis, see e.g. Barany and Merrifield, *Solid-Phase Peptide Synthesis*, pp 3–284 in *The Peptides:* Analysis, Synthesis Biology, Vol. 2: *Special Methods in Peptide Synthesis*, Part A.

Preferably, the proteins, peptides and polypeptides according to the invention are synthesized using recombinant DNA methodology, which generally involves creating a DNA sequence that encodes the protein or peptide, placing the DNA in an expression cassette under the control of a particular promoter, expressing the protein or peptide in a host, isolating the expressed protein or peptide and, if required, renaturing the product Once expressed, the recombinant peptides or proteins can be purified according to standard procedures in the art. Thus, another aspect of the present invention is a vector, such as a virus or a plasmid, comprising a nucleic acid according to the invention. Further, the invention also encompasses a recombinant cell transformed or transfected with the said vector expressing the present protein or peptide as well as a recombinant cell expressing the present antibody, which will be defined in more detail below. Vectors encoding the peptides and proteins according to the invention are useful in expressing those molecules to provide immunogens for antibody production. The vectors according to the invention are also useful for transforming cells in vitro or in vivo to express the present peptides and proteins. Cells expressing any one of the present nucleic acids such as the gene defined by SEQ ID NO 1, may be used in a wide variety of contexts and are also within the scope of the present invention. Such cells may be eucaryotic or procaryotic.

The proteins and peptides according to the invention can be used as antigens for raising antibodies against the same. Consequently, the invention also encompasses an antibody which specifically binds a peptide according to the invention. Such antibodies are useful for immunoassays, e.g for the isolation of peptides or polypeptides. The peptides according to the invention may also be used in assays, such as amplification specific assays, immunological assays etc.

The antibodies according to the invention may be monoclonal or polyclonal and include individual, allelic, strain or species variants, or fragments thereof, both in their naturally occurring (full-length) forms and recombinant forms. Additionally, the antibodies are raised to the present peptides or polypeptides in either their native configuration or in non-native configurations. Anti-idiotypic antibodies can also be generated. Many methods of making antibodies are known to persons skilled in the art. For techniques for preparing monoclonal antibodies, see e.g. Stiites et al (eds.), *Basic and Clinical Immunology* (4th ed), Lange Medical Publications, Los Altos, Calif., and references cited therein. For techniques that involve selection of libraries of recombinant antibodies in phage or similar vectors, see e.g. Huse et al. (1989) *Science* 246:1275–1281.

The molecules according to the invention may be used in pharmaceutical preparations, especially for the treatment and/or prevention of angiogenesis related disorders. Accordingly, the invention relates to a peptide, polypeptide, protein or antibody according to the invention for use as a medicament as well as to the use of said molecules in the manufacture of a medicament directed towards an angiogenesis related disease or disorder. The invention also relates to a pharmacological preparation comprising a molecule according to the invention together with a pharmaceutically acceptable carrier. The molecules used as medicaments according to the invention may be anyone of the above described peptides, polypeptides, proteins or antibodies as well as any novel substance identified in a screening method using the same and described above.

Accordingly, the most preferred use of the present molecules is in assays, wherein novel substances are screened for. Compounds may be identified which exhibit similar antangiogenic effects as angiostatin and/or kringle 5, but which are smaller, more efficient and preferably exhibits a longer half time in a human or animal body than angiostatin. The shorter half time may be due to a lower tendency to be degraded by proteases. When an organic compound is designed, a molecule according to the invention is used as a "lead" compound. The design of mimetics to known pharmaceutically active compounds is a well known approach in the development of pharmaceuticals based on such "lead" compounds. Mimetic design, synthesis and testing are generally used to avoid randomly screening a large number of molecules for a target property.

Thus, such novel molecules are preferably used as medicaments that may be administered in much lower doses than angiostatin, and which may be administered less frequently, such as e.g. once every fourteen days, which is to be compared to the half time of angiostatin which is about ten times shorter. In a particular embodiment, the novel molecules identified by the screening methods according to the invention are low molecular weight organic molecules, in which case a pharmaceutical preparation may be prepared thereof for oral intake, such as in tablets.

The pharmaceutical preparations according to the invention may however be prepared for any route of administration, e.g oral, intravenous, cutaneous or subcutaneous, nasal, intramuscular or intraperitoneal. The nature of the carrier or other ingredients will depend on the specific route of administration. (Examples of techniques and protocols that are useful in this context are inter alia found in Remington's Pharmaceutical Sciences, 16th edition, Osol, A (ed.), 1980.)

The dosage of these low molecular weight compounds will depend on the disease state or condition to be treated and other clinical factors such as weight and condition of the human or animal and the route of administration of the compound For treating human or animals, between approximately 0.5 mg/Kg of body weight to 500 mg/kg of body weight of the compound can be administered.

The present compounds and methods are advantageously used in relation to all kind of angiogenesis related disorders and/or diseases, such as tumor conditions, diabetes, rheumatoid arthritis and even some inflammatory diseases, such as psoriasis, chronic inflammation of the intestines, asthma etc. It is also suggested that they may be used in order to treat and cure, or prevent, obesity.

In a particular embodiment, the present molecules are used in gene therapy. For a review of gene therapy procedures, see e.g. Anderson, *Science* (1992) 256:808–813.

A further advantageous use of the present invention is to develop methods of regulating the signalling of the present angiostatin and/or kringle 5 receptor in the body and therefore, the invention also relates to methods of treating a human or animal patient suffering from an angiogenesis related disease or disorder as well as to methods preventing such conditions.

EXPERIMENTAL

Below, the invention will be disclosed in more detail with reference to the drawings.

All references in the present disclosure and above are hereby incorporated in the present application.

Evidence that Angiostatin Binds to Endothelial Cells

By competitive binding assays between angiostatin and the angiogenic factors, VEGF and bFGF, the present inventors have shown that angiostatin does not affect the ligand-receptor interaction of these molecules. The same level of binding could be detected in the presence or absence of unlabeled angiostatin. Thus, it can be ruled out that angiostatin acts by blocking angiogenic factors interaction with endothelial cells.

The direct binding of angiostatin and its precursor plasminogen has been studied by binding assays using iodinated proteins and analyzing their interaction with bovine microcapillary endothelial cells, see FIG. 1.

In particular, human angiostatin (kringle domains 1–4) or plasminogen was labeled with iodine 125 by the Iodogen method according to the protocol of the manufacturer (Pierce Inc.). The labelled protein was then purified on a G50 sepharose column (Pharmacia Inc.) The specific activity was estimated at 90 000 cpm/ng protein. For binding assays, bovine capillary endothelial cells were grown to confluency in 12 well plates. The cells were washed with PBS containing 1 mg/ml bovine serum albumine (BSA). The cells were then incubated with 10 ng/ml radio-labeled angiostatin or plasminogen. The binding was competed with increasing concentrations of unlabeled ligand. Cells were incubated on ice for 2 hours. Cells were then washed five times with PBS+1 mg/ml BSA. The cells were lysed with 1% Triton X100 in PBS and radioactivity was measured in a gamma counter. Dissociation constant and receptor numbers were estimated using the RBINDING program (van Zoelen E J. Anal. Biochem. 1992 Feb. 1;200 (2):393–9).

Identification of Angiostatin Binding Molecules Using the Yeast Two Hybrid System Angiostatin retains activity even after reduction, suggesting that three dimensional folding is not vital for binding and activity. This favours screening procedures wherein a large number of clones may be screened although protein refolding may be less accurate.

Figure 2:
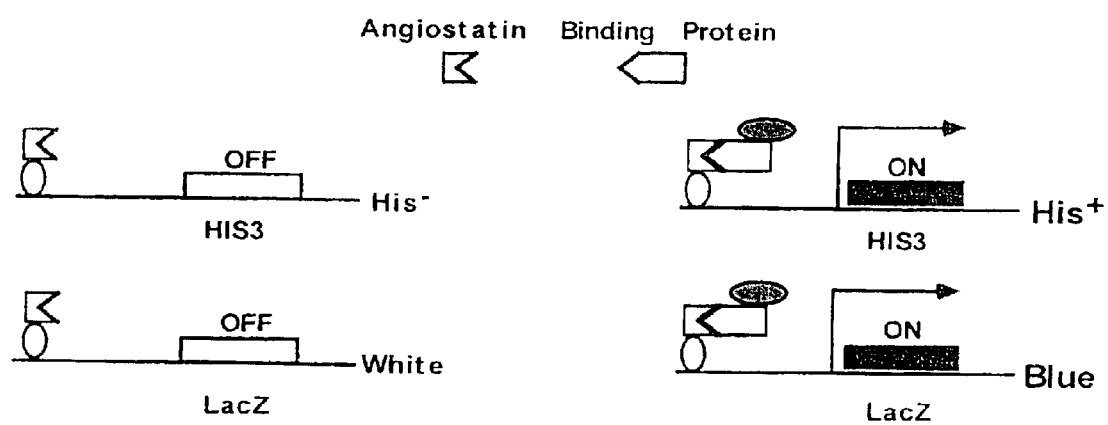
FIG. 2 illustrates activation of His3 and LacZ in the yeast two hybrid system upon binding of angiostatin binding protein.

The yeast two hybrid system was employed to screen for molecules that bind kringle domains 1–4 of plasmninogen. This is further disclosed below with reference to FIG. 2 Approximately 2×10$^6$ clones from a two hybrid CDNA library from human term placenta (Stratagene) were screened. Positives clones were identified in the following way:

(1) Screening under selective conditions (His-, Leu- and Trp-) generated 37 positive clones in yeast strain CG1945.

(2) Seven out of 37 clones displayed high β-galactosidase activity after incubation with ONPG (SIGMA) at 30° C. for 2 h.

(3) The DNA from the seven colonies that contained high β-gal activity was purified and retransfected into yeast strain Y190. Three out of the seven colonies retained activity in the new yeast strain. Sequencing analysis of these clones revealed that they were derived from the same gene.

Figure 3:
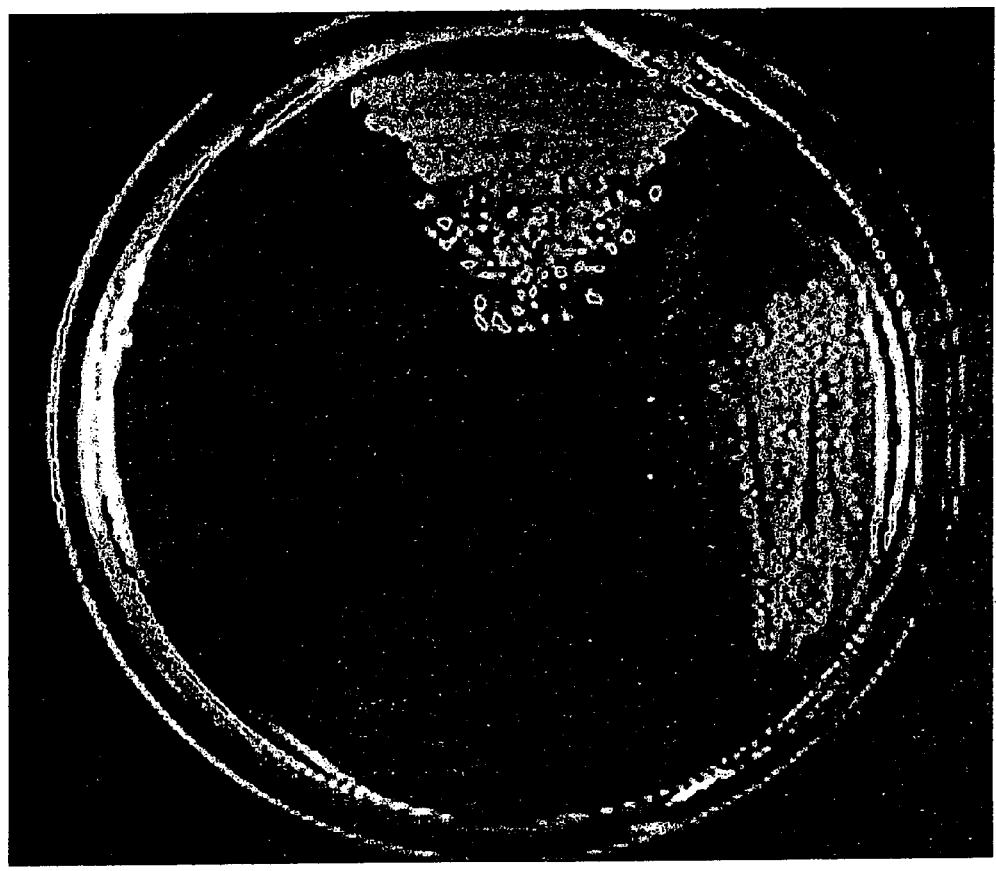
FIG. 3 shows the growth of positive yeast clones under selective conditions.

(4) Growth in the presence of 50 mM 3-aminotriazol (FIG. 3) as well as β-gal activity (see table below) was assessed in Big 3 clones and compared to positive and negative controls.

| Binding Domain | Activation Domain | β-Gal Activity |
|---|---|---|
| Angiostatin + Binding Domain | Big3 – Activation Domain | 15 u |
| Angiostatin + Binding Domain | Activation Domain alone | <0.04 u |
| Binding Domain alone | Big3 – Activation Domain | 0.07 u |
| p53 + Binding Domain | Big3 – Activation Domain | 0.05 u |
| p53 + Binding Domain | SV40LT – Activation Domain | 90 u |

Sequence of Big 3 (Angiostatin-Binding Domain)

After isolation of the big 3 clone from a placenta yeast two-hybrid library (Stratagene, Inc.), we directly sequenced the cDNA insert from the pGAD activation domain vector with GAL4 AD sequencing primers. The cDNA insert was recloned into pUC18 vector using EcoR1 sites from adaptors and sequencing was repeated using universal and reverse primers. Sequences were analyzed in an ALF automated sequencer (Pharmacia). The sequence of Big 3 is shown in SEQ ID NO. 4.

Expression and Purification of Big3 and Big3-GST Fusion Protein

Big3 sequence has been expressed in *E. coli* as fusion protein with the glutathione S-transferase (GST) domain from *Schistosoma japonicum*.

Vector Construction:

Big3 fragment (429 bp) was obtained by PCR amplification using pUC18-Big3 plasmid as template. Primer sequences were:

BamHI-NH$_2$ 5' TAC GGA TCC GAA TCG AAC AAA ACT GCA GCT G 3' (SEQ ID NO. 5)

XhoI-COOH 5' ATA CTC GAG TCA TGG AGC TGG AGT TGG AGC CA 3' (SEQ ID NO. 6)

The cycling protocol used was:

| 94° C. 3', 60° C. 1', 72° C. 1' | 1 cycle |
| 94° C. 30", 60° C. 1', 72° C. 2' | 30 cycles |
| 94° C. 30", 60° C. 1', 72° C. 5' | 1 cycle |

Taq Polymerase: Native Pfu DNA Polymerase (Stratagene)

PCR fragment was digested with BamHI and XhoI, purified and ligated to PGEX-6P-2 plasmid (Pharmacia Biotech) digested with the same restriction enzymes. Ligation mixture was used to transform XL1-Blue cells (Stratagene). Recombinant plasmids were verified by restriction analysis and automated sequencing.

Expression and Purification:

DH5α cells (Clontech) were transformed with one verified clone, named pGEX-Big3, and induced for 6 hours, room temperature with 0.1 mM IPTG.

The fermentation broth was centrifuged at 4000×rpm 15 min and the cell pellet was resuspended in 10% w/v of lysis buffer (50 mM TRIS.HCl pH 8.0, 100 mM NaCl, 20 mM DTT, 1 mM EDTA, protease inhibitor mix), and lysed by sonication. The total lysate was centrifuged at 15000×g for 20 min at 4° C. The clarified supernatant was applied to a Glutathione-Sepharose column (1 ml for 20 ml of lysate) preequilibrated with lysis buffer. The resin was washed with 10 column volumes (CV) of lysis buffer and the fusion protein was eluted with 3 CV of elution buffer (100 mM TRIS.HCl pH 8.0 20 mM reduced glutathione).

GST-Big3 protein can be cleaved by incubation of the glulathione-Sepharose bound fusion protein with 20 ul/ml resin of PreScission protease in PS buffer containing 50 mM TRIS.HCl pH 7.0, 100 mM NaCl, 1 mM EDTA, 1 mM DTT, 1 mM PMSF.

The eluted proteins behave like a single peak in rp-HPLC (10–90% gradient of acetonitrile in water plus 0.1% TFA), show the expected molecular size by mass analysis (electrospray) and the correct NH2 sequence. In SDS-PAGE a contaminant appears at the apparent MW of 80 kD; it was demonstrated to be DnaK, a bacterial chaperone, which can be eliminated running an ion exchange chromatography on a HiTrapQ column.

The yields obtained from 1 liter of fermentation are about 10 mg of GST-Big3 fusion protein and about 3 mg of the cleaved Big3.

In Vitro binding of Recombinant GST-Tagged Big 3 to Angiostatin

The protocol used for binding is described here below.

One colony of pGEX-Big3 transformant was inoculated into 10 ml LB medium plus ampicillin and grown overnight at 37° C.

The overnight culture was diluted 1:10 into 100 ml fresh medium and after 1 hour of incubation at 37° C., IPTG was added to a final concentration of 0.5 mM and incubation continued for 3 to 7 hours.

The culture was then centrifuged at 5000 g for 10 minutes, the pellet was resuspended in 3–5 ml of ice-cold PBS and cells were lysed by sonication. Triton X100 was added to a final concentration of 0.5–1% and 1.5 ml aliquots of the suspension were centrifuged at 14000 rpm for 10 minutes.

0.1–0.3 ml of 50% slurry of glutathione-agarose.beads were added to the supernatant and mixed for 3–5 hour at 4° C. The beads were then collected by centrifugation and washed 5 times with ice-cold PBS and 2 times with binding solution (B.S.) consisting of: 50 mM Tris pH7.5, 150 mM NaCl, 0.5 mM EDTA, 1 mM DTT, 1 mM PMSF).

Binding assay: 0.7 ml B.S., 0.1% calf serum, 500 ng angiostatin were mixed with 30–50 μl 50% slurry of Big3-immobilized glutathione-agarose beads for 1–3 hour at 4° C.

The resin was washed 5–7 times with ice cold B.S., then used for Western blot analysis using anti-human plasminogen antibodies (Dako Inc.).

Figure 4:
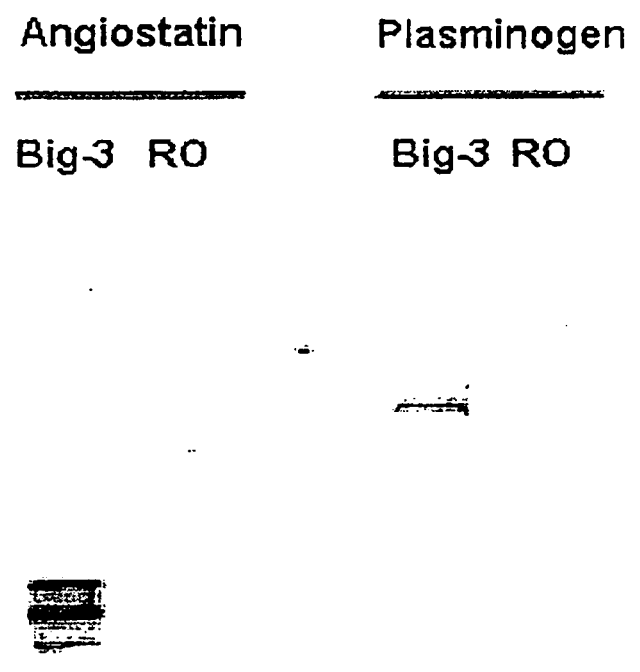

FIG. 4 shows how purified recombinant Big 3 binds angiostatin in vitro. Interestingly, binding of plasminogen could also be detected, but only after reduction of disulphide bonds by treating it with DTT.

Cloning of Full-Length Sequence

Figure 5:
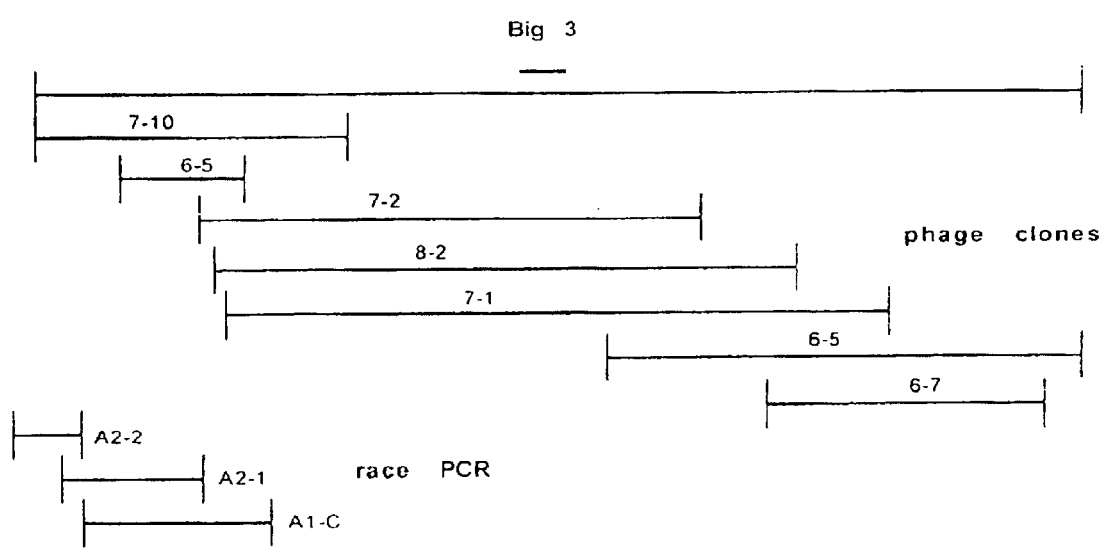
FIG. 5 is a map over "Big-3".

FIG. 5 illustrates the scheme for cloning the full-length sequence of ABP-1. The whole gene was cloned by screening a placenta cDNA phage library with a Big3 probe (with repetitive sequences removed) together with 5' RACE PCR (Gibco) using mRNA from human umbilical cord endothelial cells. The full sequence of the cDNA clone is disclosed in SEQ ID NO. 1, whereas the encoded protein is shown in SEQ ID NO. 2. Details of the experimental protocol are as follows.

10 million clones of a placenta lambda phage library (Stratagene, Inc.) were screened using a HinfI fragment of Big 3 as probe. DNA isolation and Southern blot procedures were performed according to established protocols (Sambrook et al 1989). We isolated 5 clones (7-1, 7-2, 8-2, 9-3, 9-5) with sequences that overlap with Big3. The 5'-sequence of the 7-2 clone was used for designing Gene-Specific Primers (GSP) for 5'RACE PCR (Gibco Life technologies, Inc.). mRNA isolated from Human umbilical cord endothelial cells was used to identify 5' sequences.

Primers used for the first RACE PCR:

Primers: GSP1-(5' to 3') GCTGACAGTTGCCCT-GACGCTGCT (SEQ ID NO. 10)

GSP2-(5' to 3') CGGAGACGGTGCTCTAGCTGCTCA (SEQ ID NO. 11)

GSP3-(5' to 3') TCCTTCCAACTCTTGCCTCAAGT-TCCG (SEQ ID NO. 12)

RACE procedures have been used for amplification and cloning unknown sequences between the GSP2 and GSP3 and the 5'-end of the mRNA ABP-1. This sequence was then used to design new primers for the next set of RACE RCR:

Primers: GSP1-(5' to 3') GGTGGCAGCGGACAGGCAG-GATAC (SEQ ID NO. 13)

GSP2 GAGGCGGAGAGAACTAAGAGAAGA (SEQ ID NO. 14)

GSP3 GAGCGGAGATGGAGGAGTAATTCA (SEQ ID NO. 15)

Figure 6:
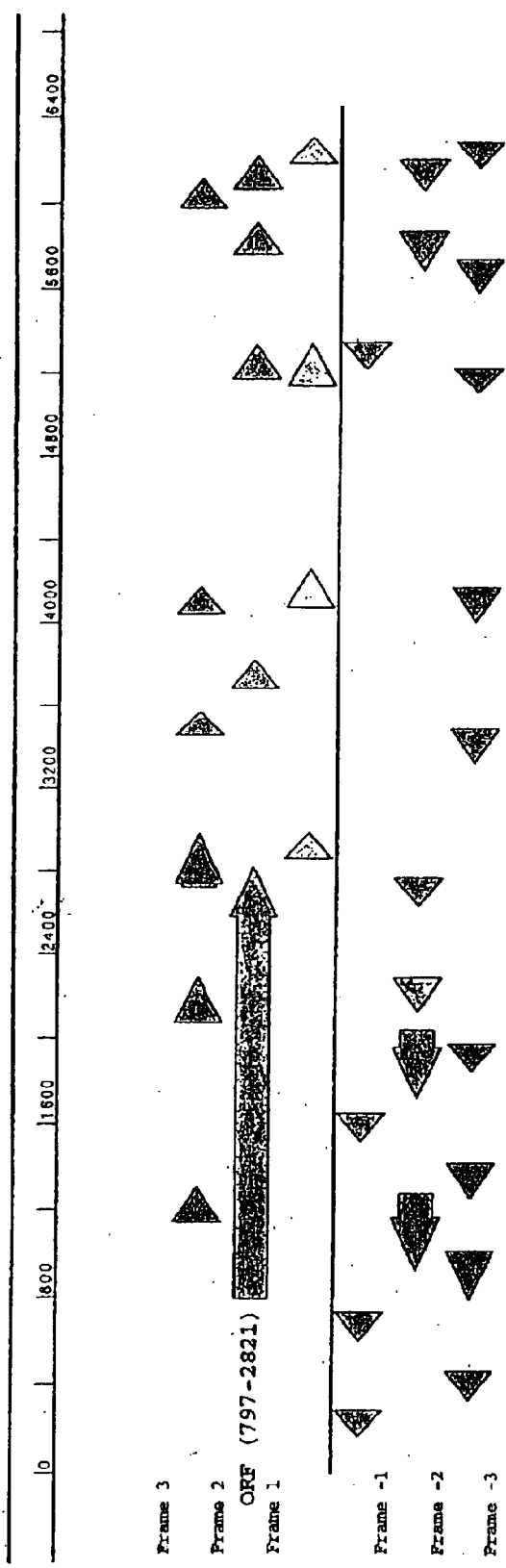
FIG. 6 shows the open reading frame (Frame 2) of the gene encoding the angiostatin receptor according to the invention. The other possible frames do not produce any putative protein

Clones A2-2, A2-1 and A1-C with overlapping sequences were isolated. The A2-1 sequence was used as probe for the second screening of the placenta phage library. From this screening we isolated another 2 clones (7-10 and 6-5). As shown in FIG. 6, of the six possible frame the only one producing a complete open reading frame is frame 2, yielding a putative protein of 675 amino acid residues.

mRNA Expression Pattern

Figure 7:
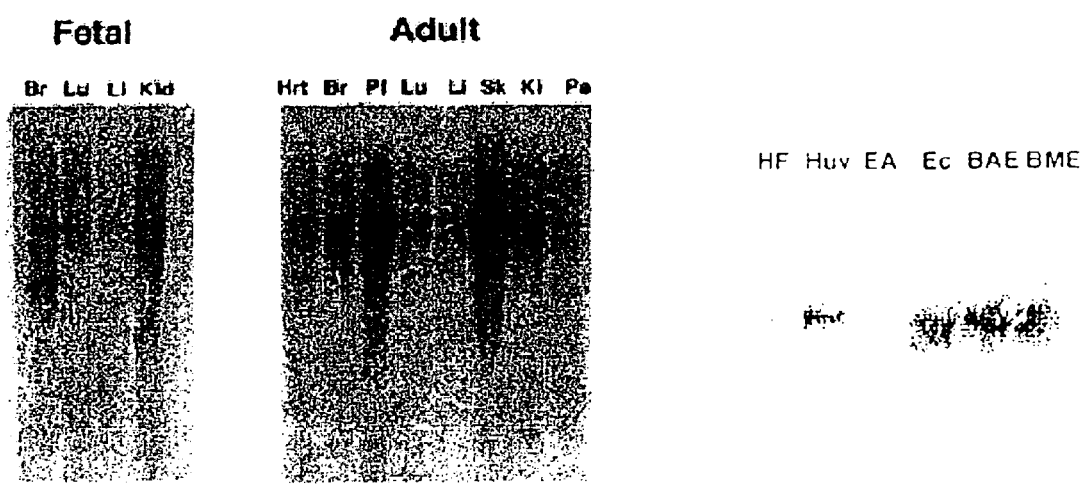
FIG. 7 shows the expression patterns of fetal and adult mRNA as well as endothelial cells.

A commercially (Clontech, Inc.) obtained multiple human adult and fetal tissue (#7760-1 and #7756-1) mRNA blots (2 mg mRNA/well) was probed for ABP-1. The blots were hybridized with the ExpressHyb hybridization solution (Clontech, Inc.) according to the protocol of the manufacturer. The blots were probed with the 7-2 5 PstI fragment. FIG. 7 shows the results of the experiment; sizes are 9.5 and 7.5 kb.

ABP-1 was also detected in human umbilical cord, bovine aortic and bovine microcapillary endothelial cells. Little or no expression was detected in the immortalized endothelial cell-line EaHy926 and in human fetal fibroblasts. Neither of the cell lines respond to angiostatin or exhibit any binding of FITC-labeled angiostatin.

Real Time RT-PCR

The 5' nuclease assay (TaqMan assay) uses a nonextendable oligonucleotide hybridization probe (TaqMan Probe). The TaqMan probe consists of an oligonucleotide with a 5'-reporter dye and a 3'-quencher dye. When the probe is intact, the proximity of the reporter dye to the quencher dye results in suppression of the reporter fluorescence, primarily by a Foster-type energy transfer. During PCR, forward and reverse primers hybridize to a specific sequence of the target DNA. The TaqMan probe hybridizes to a target sequence within the PCR product. The Taq Polymerase cleaves the TaqMan probe with its 5'-3' nuclease activity. The reporter dye and quencher dye are separated upon cleavage, resulting in increased fluorescence of the reporter.

Real Time RT-PCR Analysis

RNA Preparation

Isolation and purification of total RNA from tissues and cells listed below was performed using the Ultraspec RNA isolation system (Biotex).

| HDMEC/2 | h. dermal microvascular EC | poly A+ |
|---|---|---|
| A2780 | h. ovarian carcinoma | TOTAL |
| A375 | h. melanoma | TOTAL |
| HDF | H. dermal fibroblasts | TOTAL |
| HELA | h. cervix carcinoma | TOTAL |
| DU145 | h. prostate carcinoma | TOTAL |
| HUVEC | h. umbelical vein EC | TOTAL |
| ECV304 | immortalized EC | TOTAL |
| CEM | h. acutelymphobl. leuk. | TOTAL |
| K562 | h. erythroleukemia | TOTAL |
| JURKAT | h. acuteT-cellleukemia | TOTAL |
| THP-1 | h. monocyte (acute leu) | TOTAL |
| EaHy926 | h. dermal cells | TOTAL |
| S35/K9 | human colon cancer | TOTAL |
| Brain | human normal tissue | TOTAL |
| Colon | human normal tissue | TOTAL |
| Prostate | human normal tissue | TOTAL |
| Skel. Muscle | human normal tissue | TOTAL |
| Uterus | human normal tissue | TOTAL |
| Placenta | human normal tissue | TOTAL | cDNA Synthesis

The RT reaction was performed using TaqMan Reverse Transcription Reagent (PE Applied Biosystems) with Random hexamers, as RT primers. The reaction volume for Reverse Transcription step was 100 μl and the total RNA amount was 1 μg for sample.

The RT was performed using the following cycling parameter:

10' at 25° C.

45' at 48° C.

5' at 95° C.

PCR Reaction

After a primer concentration optimization, the PCR reaction on 10 ng of the CDNA was performed using TaqMan Universal PCR Master Mix (PE Applied Biosystems) and the following oligonucleotides ABP-1 Forward Primer: 5' GTTTGACCTGCAATCCA-GACAA 3' (SEQ ID NO. 7) Final concentration 300 nM ABP-1 Reverse Primer: 5' CCCAGGATCTGAATGG-GAGTT 3' (SEQ ID NO. 8) Final concentration 900 nm ABP-1 TaqMan Probe: 5' (FAM dye)-CAGATGGGCCTGTGTTCCACTCCAA-(TAMRA dye) 3' (SEQ ID NO. 9) Final probe concentration 200 nM The cycling protocols was:

2' at 50° C.; 10' at 95° C. 1 cycle

15" at 95° C.; 1' at 60° C. 40 cycles

Relative Quantitation of Gene Expression

The Comparative method use an arithmetic formula to achieve the result for relative quantitation without need for Standard curve.

Figure 8:
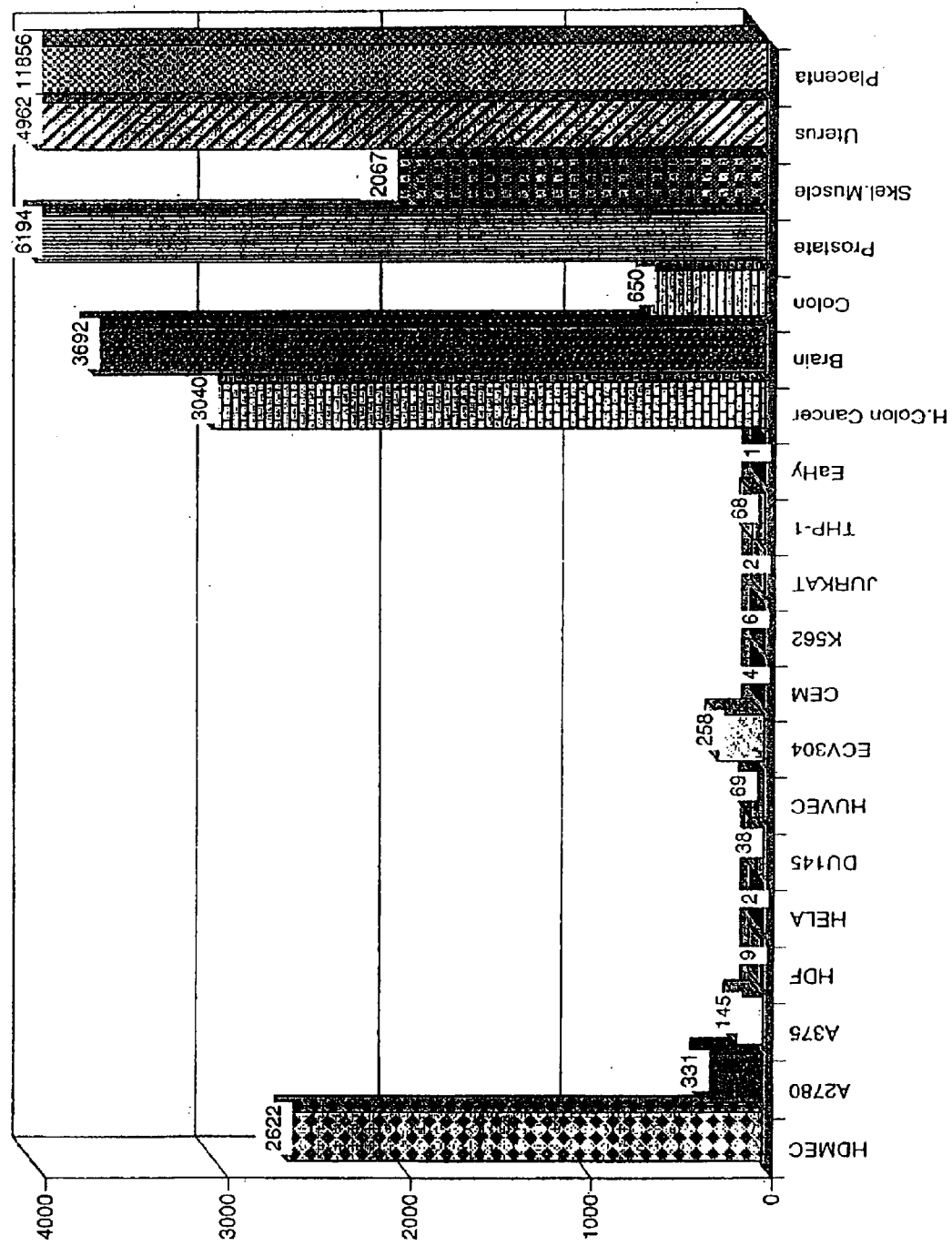
FIG. 8 shows the relative quantitation of ABP-1 gene expression in different tissue. See experimental section for more details.

The result, depicted in FIG. 8, indicate how many fold the sample X expresses the target relative to the Calibrator which is the sample that shows the lowest level of expression of the target. In this experiment EaHY926 sample was chosen as calibrator.

Antibodies Against Big-3

For immunisation of New Zealand White rabbits, 100 micrograms of Big3-GST fusion protein were dissolved in 1 ml phosphate buffered saline (PBS) homogenised with 1 ml of Freund's Complete Adjuvant (Gibco). The resulting emulsion was injected subcutaneously on day 0 and this treatment was repeated on days 15 and 28. Blood was removed from rabbits on day 35, allowed to coagulate overnight at 4° C., and the resulting serum stored at −20° C.

For purification of specific antibodies, resin-immobilised ligand was produced as follows: Big3 polypeptide was diluted in 0.1M sodium bicarbonate. 0.5 M NaCl, pH8.3, at a concentration of 5 mg/ml in a total volume of 2 ml. This was reacted for two hours at room temperature with 2 ml of cyanogen bromide-activated Sepaharose CL-4B resin (Sigma Chemical Co. St Louis, Mo.). After reaction, the resin was washed three times in 10 volumes of 100 mM Tris, 500 mM NaCl, pH 7.5. Immune serum was incubated with the affinity resin for two hours at 4° C., after which resin was washed in a 5 ml glass chromatography column (Bio-Rad, Richmond Calif.) for with 25 volumes of 100 mM Tris, 500 mM NaCl, pH 7.5. Specific antibodies were eluted in 1 ml aliquots with 100 mM Glycine/HCl, pH 2.8. Elution of antibody was followed by monitoring the optical density at 280 nM (OD280), and fractions with an OD280 of greater than 1 were pooled and dialysed (Slide-A-lyzer cassettes, Pierce) for 36 hours at 4° C. against 1 liter PBS, with three changes of buffer.

Binding and Signalling of Angiostatin via the ABP-1 Protein

Figure 9A:
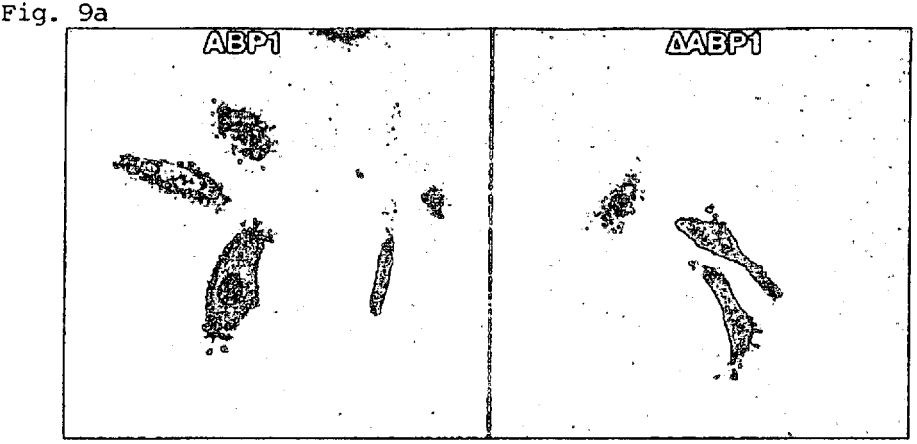
FIG. 9 illustrates (A) the cellular localization of GFP-tagged ABP-1 receptor in transiently transfected HeLa cells and (B) the reorganization of GFP-labeled ABP-1 after incubation with angiostatin.
FIG. 9C shows the binding of angiostatin to ABP-1. See the experimental section for more details.
FIG. 9D is an immunostaining of ABP-1 in Human umbilical cord endothelial (HUVE) cells together with staining against F-actin with rhodamin-labelled phalloidin. ABP-1 is localized in focal adhesions and membrane ruffles (arrows).
Figure 9B:
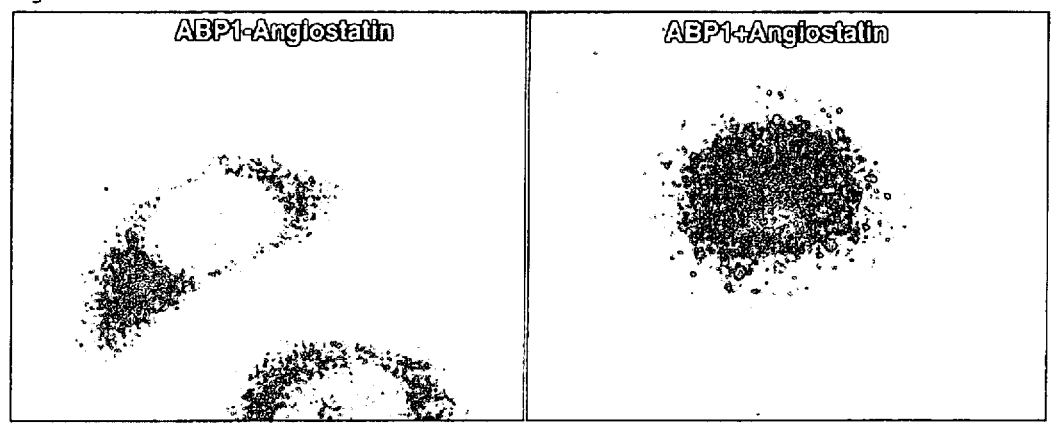

FIGS. 9A and 9B show data of binding of FITC-labeled angiostatin to ABP-1 transfected HeLa and EaHy926 cells transfected with the vector control. In particular FIG. 9A shows the cellular localization of ABP-1 fused to green fluorescent protein (GFP) in transiently transfected cells. The protein can be detected in the endoplasmic reticulum and the cell membrane. DABP-1 contains a 500 bp deletion in the 5'end of the gene, which disrupts the previously described localization of ABP-1.

FIG. 9B shows HeLa cells transfected with ABP-1 GFP. Incubation with 2.5 mg of angiostatin for 60 minutes at 0° C. and subsequent incubation for 15 minutes at 37° C. induces internalization of ABP-1-GFP.

Figure 9C:
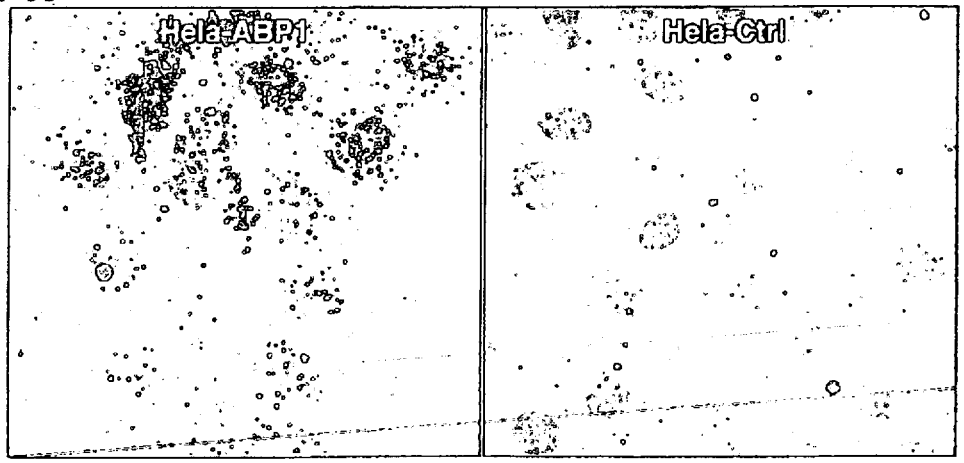

FIG. 9C shows the binding of angiostatin to ABP-1. We have shown that fluorescein isothiocyanate (FITC)-labelled angiostatin binds specifically to endothelial cells (data not shown). We have transfected HeLa cells with either the ABP-1 expression construct or the vector control (p RC/CMV, In Vitrogen, Inc.). We incubated live HeLa cells FITC-labelled angiostatin (10 ug/ml) in DMEM+10% fetal calf serum at 0° C. for 60 minutes. The cells were then incubated at 37° C. at 15 minutes to aggregate bound angiostatin. Binding was analyzed with a fluorescent microscope. Binding of angiostatin was detected in ABP-1 transfected cells but not in the vector control.

Figure 9D:

FIG. 9D shows immunostaining of ABP-1 in Human umbilical cord endothelial (HUVE) cells together with staining against F-actin with rhodamin-labelled phalloidin.

Immunostaining Protocol:

HUVE cells were fixed in 4% formaldehyde, washed in PBS and preblocked in 5% horse serum. The blocking solution was removed and replaced by rabbit polyclonal antibodies against the angiostatin-binding domain Big3 diluted in 5% horse serum. Positive staining was visualized with a fluorescence-labeled secondary antibody (Dako, Inc.). Rhodamin-conjugated phalloidin (Molecular Probes, Inc.) was stained simultaneously with the secondary antibody (after permeabilization with 1% triton X100 for 1 minute). Rabbit polyclonal antibodies against green fluorescent protein was used as a negative control. In addition no positive staining could be detected in human fibroblasts.

As can be seen in FIG. 9D, ABP-1 is localized in focal adhesions and membrane ruffles (arrows).

In Vitro Kinase Data

Huve cells were plated subconfluent in 5 cm Petri dishes. Angiostatin was added at 2.5 mg/ml at different time points the following day. All plates including controls were harvested simultanously. The cells were rinsed in ice cold PBS and incubated in 1 ml lysis buffer. The cells were transferred to an eppendorf tube and centrifuged at 14000 rpm for 5 minutes at 4° C. The supernatant was transferred to another eppendorf tube and 2 $\mu$g of Big 3 rabbit polyclonal antibodies was added. The samples were incubated for 60 min. at 4° C. and subsequently 50 $\mu$l of a protein A sepharose (Pharmacia, Inc.) slurry was added and incubated for another 60 min. in a rotating incubator. The immunoprecipitates were collected by brief centrifugation and washed two times in lysis buffer, once in washing buffer and once in kinase buffer. Residual buffer was removed with a syringe. 25 $\mu$l of kinase buffer was added to each tube together with 1 $\mu$Ci gammaATP (Amersham, Inc.). The samples were incubated at R.T. for 20 minutes. The reaction was stopped by adding 2×SDS PAGE sample buffer. The samples were boiled under denaturing conditions and subsequently analyzed by SDS PAGE.

Figure 10:
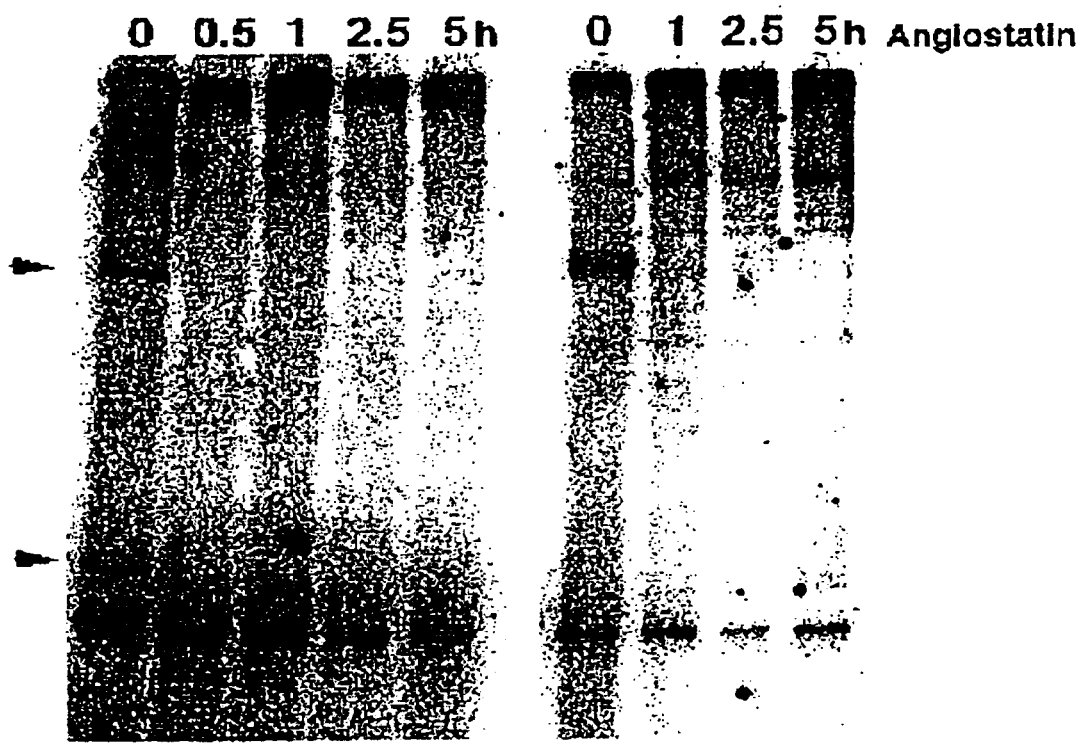
FIG. 10 illustrates the down regulation of ABP-1 associated kinase activity after addition of angiostatin.

The data illustrated in FIG. 10 show that addition of angiostatin downregulates ABP-1 associated kinase acivity within 30 minutes. This is direct proof that angiostatin affects signalling pathways that are mediated by ABP-1.

ABP-1 Mediates Angiostatin-Induced Focal Adhesion Kinase Activity.

Figure 11:
FIG. 11 is an autoradiography of an SDS-PAGE demonstrating that ABP-1 mediates angiostatin-induced focal adhesion kinase activity. See experimental section for more details.

The data illustrated by FIG. 11 show that addition of 2.5 $\mu$g/ml of angiostatin upregulates FAK activity within 1 hour after addition.

EaHy926 cells were plated subconfluent in 5 cm Petri dishes. Angiostatin was added at 2.5 $\mu$g/ml at different time points the following day. All plates including controls were harvested simultaneously. The cells were rinsed in ice cold PBS and incubated in 1 ml lysis buffer. The cells were transferred to an eppendorf tube and centrifuged at 14000 rpm for 5 minutes at 4° C. The supernatant was transferred to another eppendorf tube and 1 ug of FAK monoclonal antibody (Transduction Lab. Inc.) was added. The samples were incubated for 60 min. at 4° C. and subsequently rabbit anti-mouse IgG+50 $\mu$l of a protein A sepharose (Pharmacia, Inc.) slurry was added and incubated for another 60 min. in a rotating incubator. The immunoprecipitates were collected by brief centrifugation and washed two times in lysis buffer, once in washing buffer and once in kinase buffer. Residual buffer was removed with a syringe. 25 ∥l of kinase buffer was added to each tube together with 1 $\mu$Ci γATP (Amersham, Inc.). The samples were incubated at R.T. for 20 minutes. The reaction was stopped by adding 2×SDS PAGE sample buffer. The samples were boiled under denaturing conditions and subsequently analyzed by SDS PAGE.

As can be seen in FIG. 11, addition of angiostatin upregulates FAK activity within 1 hour. It should be noted that EaHy926 cells are not expressing ABP1 as demonstrated by reverse transcriptase PCR analysis.

What is claimed is:

1. An isolated protein that is a receptor for an N-terminal fragment of plasminogen comprising kringle domains 1–4 and wherein said protein comprises a sequence having sequence homology equal to or greater than 98% to SEQ ID No: 4.

2. An isolated protein that is a receptor for an N-terminal fragment of plasminogen comprising kringle domains 1–4 and wherein said protein comprises SEQ ID No: 4.

3. The isolated protein according to claim 2 that has sequence homology equal to or greater than 80% to SEQ ID Nos: 2 or 3.

4. The isolated protein according to claim 2 that has sequence homology equal to or greater than 95% to SEQ ID Nos: 2 or 3.

5. The isolated protein according to claim 2 that has sequence homology equal to or greater than 98% to SEQ ID Nos: 2 or 3.

6. The isolated protein according to claim 2 that has sequence homology equal to or greater than 99.6% to SEQ ID Nos: 2 or 3.

7. The isolated protein according to claim 2, wherein said protein has angiogenic activity.

8. The isolated protein according to claim 3, wherein said protein has angiogenic activity.

9. The isolated protein according to claim 4, wherein said protein has angiogenic activity.

10. An isolated protein that is a receptor for an N-terminal fragment of plasminogen comprising kringle domains 1–4 and wherein said protein has sequence homology equal to or greater than 98% of SEQ ID No: 2.

11. The isolated protein according to claim 10 wherein said protein is SEQ ID No: 2.

12. The isolated protein according to claim 10 wherein said protein is SEQ ID No: 3.

13. A method for treating an angiogenesis-related disease or disorder comprising administering an effective amount of a protein of any one of claims 1–12 to a patient in need thereof.

14. A method for manufacturing a composition for the treatment of an angiogenesis-related disease comprising mixing a protein according to any one of claims 1–12 with a suitable pharmaceutical carrier.

15. A composition comprising a protein according to any one of claims 1–12 together with a pharmaceutically acceptable carrier.

* * * * *

SEQUENCE LISTING

<160> NUMBER OF SEQ ID NOS: 15

<210> SEQ ID NO 1
<211> LENGTH: 6463
<212> TYPE: DNA
<213> ORGANISM: Homo sapiens -continued

```
<220> FEATURE:
<221> NAME/KEY: CDS
<222> LOCATION: (797)..(2824)

<400> SEQUENCE: 1
```

| | |
|---|---:|
| ccaggagctg ccttggcagt cacgcccctt ccttccgagg agctttctgg ctgcctaaac | 60 |
| tggtagaccc cctgaattac tcctccatct ccgctctctt tcgcctcctc ttctcttagt | 120 |
| tctctccgcc tcccctcaa ctaccaccac ctccagtcag tctcgcctcc ggctatccgc | 180 |
| tgctccaccc tctggcccgg tatcctgcct gtccgctgcc accaaggaga gcccggacgg | 240 |
| agcagcgagg aggggagcag ccgggagttg gggcttcccc cctgcccatc cctggccgct | 300 |
| ggcccgggac cgaagccact tgagcgagca gagagtcgtc accttgtctt ctttgccttc | 360 |
| agggagctgc taagaaggac aaataagata gcagagtgaa agagcttttg tctccttaga | 420 |
| aggaaggctg agaaactaaa ggccagcgca ggacatctca ttgccattgt cagccaggaa | 480 |
| ctcgcagcct cacagcccta cttcttctct gacctctggg gggtccttgc ccttgctaca | 540 |
| atctccacca tccactagat tgtctcctgc ccgacacccc ttggtcccaa accagggaga | 600 |
| ccattcagct cacctgccta ggccgcagca gcatttcctt cctaatcagg ctcaccaggg | 660 |
| ggatcattac cgtctctccc aacctggcct gagtcagcag cagcagcaac agcagcagca | 720 |
| gcaccatcat caccatcacc accaacaaca gcagcagcag cagccacagc agcagccagg | 780 |
| agaagcctat tcagct atg cct cgg gct cag cca tcc tct gct tct tat cag | 832 |
|                                      Met Pro Arg Ala Gln Pro Ser Ser Ala Ser Tyr Gln<br>                                       1             5                 10 | |
| cca gtg cca gca gac cct ttt gcc att gtt tcc aga gcc cag cag atg<br>Pro Val Pro Ala Asp Pro Phe Ala Ile Val Ser Arg Ala Gln Gln Met<br>               15                  20                 25 | 880 |
| gtt gag atc ctc tca gac gag aac cgg aac ttg agg caa gag ttg gaa<br>Val Glu Ile Leu Ser Asp Glu Asn Arg Asn Leu Arg Gln Glu Leu Glu<br>    30                  35                  40 | 928 |
| gga tgc tat gag aag gtg gca aga ctg cag aag gtg gag aca gaa atc<br>Gly Cys Tyr Glu Lys Val Ala Arg Leu Gln Lys Val Glu Thr Glu Ile<br> 45                50                  55                 60 | 976 |
| cag cgc gtc tcg gag gca tat gag aac ctc gtg aag tca tcc tcc aaa<br>Gln Arg Val Ser Glu Ala Tyr Glu Asn Leu Val Lys Ser Ser Ser Lys<br>               65                  70                 75 | 1024 |
| aga gag gcc cta gag aaa gcc atg aga aac aag cta gag ggc gag att<br>Arg Glu Ala Leu Glu Lys Ala Met Arg Asn Lys Leu Glu Gly Glu Ile<br>    80                  85                  90 | 1072 |
| cgg agg atg cat gat ttc aac agg gat ctg aga gag cgt cta gag act<br>Arg Arg Met His Asp Phe Asn Arg Asp Leu Arg Glu Arg Leu Glu Thr<br> 95                100                105 | 1120 |
| gcc aac aag cag ctt gca gag aag gaa tat gag ggg tca gag gac acc<br>Ala Asn Lys Gln Leu Ala Glu Lys Glu Tyr Glu Gly Ser Glu Asp Thr<br>        110               115                120 | 1168 |
| aga aaa acc atc tcg cag ctc ttt gca aaa aat aaa gaa agc cag cgt<br>Arg Lys Thr Ile Ser Gln Leu Phe Ala Lys Asn Lys Glu Ser Gln Arg<br>125               130                135               140 | 1216 |
| gag aag gag aag ctg gaa gcg gag ctg gcc act gcc cgt tct acc aat<br>Glu Lys Glu Lys Leu Glu Ala Glu Leu Ala Thr Ala Arg Ser Thr Asn<br>               145                150               155 | 1264 |
| gag gac caa aga cga cac atc gaa atc cga gat cag gcc ctg agt aat<br>Glu Asp Gln Arg Arg His Ile Glu Ile Arg Asp Gln Ala Leu Ser Asn<br>        160               165                170 | 1312 |
| gcc cag gcc aag gtg gta aag ctg gaa gaa gag ctg aaa aag aag caa<br>Ala Gln Ala Lys Val Val Lys Leu Glu Glu Glu Leu Lys Lys Lys Gln<br>175               180                185 | 1360 |

-continued

| | |
|---|---|
| gtg tac gtt gac aag gtg gag aag atg cag cag gcc ctt gta cag ctc<br>Val Tyr Val Asp Lys Val Glu Lys Met Gln Gln Ala Leu Val Gln Leu<br>190                              195                         200 | 1408 |
| cag gca gca tgt gaa aaa cgt gag cag cta gag cac cgt ctc cgg aca<br>Gln Ala Ala Cys Glu Lys Arg Glu Gln Leu Glu His Arg Leu Arg Thr<br>205                              210                         215                 220 | 1456 |
| cga ctg gag agg gaa ctg gaa tcc ctg aga atc cag cag cgt cag ggc<br>Arg Leu Glu Arg Glu Leu Glu Ser Leu Arg Ile Gln Gln Arg Gln Gly<br>                         225                         230                         235 | 1504 |
| aac tgt cag ccc acc aac gtt tca gaa tac aat gct gcc gca ctg atg<br>Asn Cys Gln Pro Thr Asn Val Ser Glu Tyr Asn Ala Ala Ala Leu Met<br>                240                         245                         250 | 1552 |
| gag ctc ctt cgg gag aaa gag gag agg att ctg gct ctg gaa gct gat<br>Glu Leu Leu Arg Glu Lys Glu Glu Arg Ile Leu Ala Leu Glu Ala Asp<br>255                              260                         265 | 1600 |
| atg aca aag tgg gag cag aaa tat ttg gag gag aat gtg atg aga cat<br>Met Thr Lys Trp Glu Gln Lys Tyr Leu Glu Glu Asn Val Met Arg His<br>      270                         275                         280 | 1648 |
| ttt gct ctg gat gct gct gca act gtg gct gct cag agg gac aca aca<br>Phe Ala Leu Asp Ala Ala Ala Thr Val Ala Ala Gln Arg Asp Thr Thr<br>285                              290                         295                 300 | 1696 |
| gtc atc agt cac tct cct aac acc agc tat gac aca gct cta gaa gct<br>Val Ile Ser His Ser Pro Asn Thr Ser Tyr Asp Thr Ala Leu Glu Ala<br>                    305                         310                         315 | 1744 |
| cgc atc cag aaa gag gag gaa gaa atc ttg atg gcc aat aag cgt tgc<br>Arg Ile Gln Lys Glu Glu Glu Glu Ile Leu Met Ala Asn Lys Arg Cys<br>                  320                         325                         330 | 1792 |
| ctt gac atg gag ggc agg att aag acc ctc cat gcc cag att att gag<br>Leu Asp Met Glu Gly Arg Ile Lys Thr Leu His Ala Gln Ile Ile Glu<br>                    335                         340                         345 | 1840 |
| aag gat gcc atg atc aaa gta ctc cag cag cgt tcc cgg aag gag ccg<br>Lys Asp Ala Met Ile Lys Val Leu Gln Gln Arg Ser Arg Lys Glu Pro<br>350                              355                         360 | 1888 |
| agc aag aca gag cag ctg tcg tgc atg cgg cca gcg aag tct ctg atg<br>Ser Lys Thr Glu Gln Leu Ser Cys Met Arg Pro Ala Lys Ser Leu Met<br>365                              370                         375                 380 | 1936 |
| tcc att tcc aat gct gga tca ggc ttg ctc tcc cac tca tcc acc ctg<br>Ser Ile Ser Asn Ala Gly Ser Gly Leu Leu Ser His Ser Ser Thr Leu<br>                  385                         390                         395 | 1984 |
| act ggc tcc ccc atc atg gaa gaa aag cga gac gac aag agc tgg aag<br>Thr Gly Ser Pro Ile Met Glu Glu Lys Arg Asp Asp Lys Ser Trp Lys<br>                400                         405                         410 | 2032 |
| ggg agc cta ggc att ctc ctg ggt gga gac tac cgt gct gaa tat gtc<br>Gly Ser Leu Gly Ile Leu Leu Gly Gly Asp Tyr Arg Ala Glu Tyr Val<br>                  415                         420                         425 | 2080 |
| cct tcc aca ccc tcg cct gtg cca ccc tcg act ccc ctg ctc tcg gct<br>Pro Ser Thr Pro Ser Pro Val Pro Pro Ser Thr Pro Leu Leu Ser Ala<br>430                              435                         440 | 2128 |
| cac tcc aag aca ggc agc cga gac tgc agt acc caa act gaa cgt ggg<br>His Ser Lys Thr Gly Ser Arg Asp Cys Ser Thr Gln Thr Glu Arg Gly<br>445                              450                         455                 460 | 2176 |
| acg gaa tcg aac aaa act gca gct gtt gct ccc atc tct gtt cct gct<br>Thr Glu Ser Asn Lys Thr Ala Ala Val Ala Pro Ile Ser Val Pro Ala<br>                  465                         470                         475 | 2224 |
| cca gtt gct gct gcc gcc act gct gcc gcc atc act gcc act gct gcc<br>Pro Val Ala Ala Ala Ala Thr Ala Ala Ala Ile Thr Ala Thr Ala Ala<br>                  480                         485                         490 | 2272 |
| acc atc acc acc acc atg gta gct gct gct cca gtt gct gtt gct gct<br>Thr Ile Thr Thr Thr Met Val Ala Ala Ala Pro Val Ala Val Ala Ala<br>495                              500                         505 | 2320 |

```
                                                          -continued gct gct gct cca gct gct gct gct gcc ccg tct cca gcc act gcc gct    2368
Ala Ala Ala Pro Ala Ala Ala Ala Ala Pro Ser Pro Ala Thr Ala Ala
        510                 515                 520 gct act gct gct gct gtt tct cca gct gct gct ggt cag att cca gct    2416
Ala Thr Ala Ala Ala Val Ser Pro Ala Ala Ala Gly Gln Ile Pro Ala
525                 530                 535                 540 gct gcc tct gtt gcc tca gct gct gcc gtt gct cct tct gct gct gct    2464
Ala Ala Ser Val Ala Ser Ala Ala Ala Val Ala Pro Ser Ala Ala Ala
                545                 550                 555 gct gct gct gtt cag gtt gct cca gct gct ccg gct cca gtt cca gct    2512
Ala Ala Ala Val Gln Val Ala Pro Ala Ala Pro Ala Pro Val Pro Ala
                560                 565                 570 ccg gct ctg gtt ccg gtt cca gct cca gca gcg gct cag gct tct gct    2560
Pro Ala Leu Val Pro Val Pro Ala Pro Ala Ala Gln Ala Ser Ala
        575                 580                 585 cct gct cag act cag gca cca act tca gct ccg gct gtg gct cca act    2608
Pro Ala Gln Thr Gln Ala Pro Thr Ser Ala Pro Ala Val Ala Pro Thr
590                 595                 600 cca gct cca act cca act cca gct gtg gct cag gct gag gtt cct gca    2656
Pro Ala Pro Thr Pro Thr Pro Ala Val Ala Gln Ala Glu Val Pro Ala
605                 610                 615                 620 agt cca gct acc ggt cct gga cca cat cgt ttg tct ata cca agt ttg    2704
Ser Pro Ala Thr Gly Pro Gly Pro His Arg Leu Ser Ile Pro Ser Leu
                625                 630                 635 acc tgc aat cca gac aaa aca gat ggg cct gtg ttc cac tcc aat act    2752
Thr Cys Asn Pro Asp Lys Thr Asp Gly Pro Val Phe His Ser Asn Thr
                640                 645                 650 ctg gaa aga aaa act ccc att cag atc ctg gga caa gag cct gat gca    2800
Leu Glu Arg Lys Thr Pro Ile Gln Ile Leu Gly Gln Glu Pro Asp Ala
        655                 660                 665 gag atg gtg gaa tat ctc atc taa acggccaaat caagagctgc agattatcag    2854
Glu Met Val Glu Tyr Leu Ile
670                 675 caaaaatgct tttaatcatt ttcccccttt tattggttct tgttttgagg gtgaggacaa    2914
gggttgtggg gaggggatgt tttttaacag gactttttat tggaacaatg tactacttga    2974
gtaataccat gtgaacacca gtctattttg gtatgcttag ggagtacctc taaagacaga    3034
ttaatcagaa tgtgctctaa agcttattgt ttgaatttat acgaatactg ggactgttaa    3094
caggtggcta tacatcgacg ttttcaatgt gcttaaattt gtttaaattt tccatattct    3154
agatcatttt ttattgaaga gcacagtatg tgtggaagac agtgtataac acgtagtttg    3214
gaagtgggaa gctagagaga attgagtgtg tgctgttttg tatagttact atcctgtgca    3274
gcagctggag aaagcactca cctcaggctt acaaaaggga atagtttcag gagctatgta    3334
agctggaaaa aaggtaggga gttttggggt gcagaagggt actggagcta atttttttctt    3394 ccagtttccc agctaccctg ccccagggaa ttgtgtttgt cttcatttca gtggtgcttt    3454
ggaaatggat tcttttggtt ccctcctgga ggttcataca ttcatatata tgctctggag    3514
taatttatgc atttggataa ttaatatatt gctttcagat gctgggagag tacattaact    3574
gagtgatgcg caacttcctc tctcttaggg aattagacca tcagaggcct tgatggagag    3634
ttgcatgggg tgctatatgc agacttccat ggtttgtgtg tagccatgaa cacagcttgc    3694
ttgcatttag taagaccaat cagcttagtg tttatttctt ctacagcaca gattcactgg    3754
ctgggtctcc agtctcaaat tgccaatcat ttgcaaagtg aggaaggatc tttgttgaca    3814
ggttgaatgc tttgaatttc tggtgactac tttgaaataa cttgttttgt ttgtcaaatt    3874
ctaagcatat gtcttaaaag gcattttgga ctatcacctc caagggaata gcttgagaaa    3934
```

```
cccaaagtac tatgctgcag tcgggggaga ggtggattgc agcagtatcc tcaactacct    3994
cttctcactg tcagtgacac catcttggaa tacctttggg aagcagcagg aaatgtgcat    4054
gtgggtagag atcaaaggag gcaatggctc caagccttgc cataggctg cctccaagga     4114
cacagaagga tgccagttgc cacaggtccc tgccctgtgt cacctgtctg cccttcatta    4174
aggtgagaaa tctgcagata gcatcattaa gatcagtttt aagggtata gggagggtga     4234
gggaagtggg gggtgttagg taaggttgg gggtagaggt tttgggatgt cttagttaga     4294
aaccagatta atagaagagt aggcctgata tattacatca tgagccatag tggtgggaaa    4354
gaactttagc aatatagccc tacctcctca ttttagtgat gaggaatctg agaactggag    4414
aggttcagtg acttttttgaa agtcatacaa cacagctaac cattatgcca atcaccatgc   4474
ttattttggg aaactcttta tctttttttaa attccattttt atgaaaaggc atcttcatgg  4534
tccagggaat atgtatcttg taaaatgtac ctggttggag tagcttgtcc agtcttgaca    4594
aactactgaa tttctgtctt gcctctcctt cagtgccttt taaaaggttt tcccttttct    4654
gatctgcatt tcaacataga gtcacataaa tgtcccccctg agaaaccaat cccacttctt   4714
tctaggagat tgggtatctt agataatctt ttggggttcc tctgtgagta taggaatggt    4774
atccttccta attatcttcc aaaggaatta ttttgtgtgt gtgcctgtgt gtgtgtagag    4834
acataaagga gggtgatgtg attttcagct agtcctttca cattttcaat aatgaggtaa    4894
tcatgttaca tacacattag tcctcagtta taaagtgaat ctcagataga aattaaaagt    4954
gcagttgtgt taagactctt tcatactacc ctttagtcat aaggagaaaa aaacactcaa    5014
atagtagaag cagcaagtag caaacttcag gagagctact ttctatccaa ataatttaaa    5074
aaacactttt cacctactcc tttcatggtt ataacacatt ggcagacttt ttgctggctc    5134
tgggagccat gattttaatc acattctgca aggtgacaaa tgtcatacat tccacattgt    5194
gtggtagcca tctctttaga ctcatgtgtt ttgggggaaag gaagaagttc ttggctgagt   5254
actattttga acttttccaga accctctcac accagagaca gttcttctct gttcagtttc   5314
caatccccga taatttgcta aaataacatt gtacatccaa gagagggaag aagagtatgt    5374
cagtatatta tgcagaagat agatacagcc ttttcagaag atctccacta gttttttgttc   5434
caaaaattca gtttatggg agaaatctca attagccacc ttttcacagt tgtgtggata     5494
taacatttgg gggatctttc tggactccta cctatctgtg catttaccg gcacctcagg    5554
aaaggagggt gaccaggttg tcttagcttg tactgcttgg tgatctctga ggaccttcta    5614
attcagttgt accccagtgt tccatgtata gaaaaacttc attagaacaa actttacttg    5674
atatgaaact cctattaaca gtcttttttt gaaataaaaa gtagcttgag cttttctttta   5734
aaaatcatgta tcttgattgt tgatttaatg aaggatttcc ttttaatgct gcttttgagc   5794
ttcaaggtaa taggacagca ggaacctaaa atatctgcca tcatctgcca taggaaagat    5854
acccagagac ccatcatgtt ctcttttttgt tgttacactg ttgggtgggt ataacaattg   5914
gaaaatgaac aaactgattg attgtgcaaa ctacttttta tgacaagcct aaaccctcat    5974
aatgcggcag cttaaagtgt atacatatgc actaactttg atcaattata ttctcatatc    6034
tgttagctac acagtctcct attatctcaa ttgcttatgt gcatatggaa tatgttactt    6094
aaaacgtgtg cattcttact gaaaatgttt tcaaggaag gtatcagctg tgggctaatt     6154
gccaccaatt tcagcctgcc acgattcttg gaaatatgtc ttccaagtgc catccatcat    6214
cagtaggaca agtgtcggga gtttgttat tttttttccag tagcaacgat gggttacatg    6274
gagccatgaa acctccttct ggcctcccctt gtgattaatg gcatgtgttt gtaaaatgga   6334
```

```
tagctggggt tggcagatgg ctagagaaga atcgcctttg gtttaaaatg tatgtggtcc    6394
cctaatgatt gtgaccccat tctgtaatca actgagctag ttccaataaa gttaagcagg    6454
tttaaatcc                                                            6463
```

<210> SEQ ID NO 2
<211> LENGTH: 675
<212> TYPE: PRT
<213> ORGANISM: Homo sapiens

<400> SEQUENCE: 2

```
Met Pro Arg Ala Gln Pro Ser Ser Ala Ser Tyr Gln Pro Val Pro Ala
  1               5                  10                  15

Asp Pro Phe Ala Ile Val Ser Arg Ala Gln Gln Met Val Glu Ile Leu
             20                  25                  30

Ser Asp Glu Asn Arg Asn Leu Arg Gln Glu Leu Glu Gly Cys Tyr Glu
         35                  40                  45

Lys Val Ala Arg Leu Gln Lys Val Glu Thr Glu Ile Gln Arg Val Ser
     50                  55                  60

Glu Ala Tyr Glu Asn Leu Val Lys Ser Ser Lys Arg Glu Ala Leu
 65                  70                  75                  80

Glu Lys Ala Met Arg Asn Lys Leu Glu Gly Glu Ile Arg Arg Met His
                 85                  90                  95

Asp Phe Asn Arg Asp Leu Arg Glu Arg Leu Glu Thr Ala Asn Lys Gln
            100                 105                 110

Leu Ala Glu Lys Glu Tyr Glu Gly Ser Glu Asp Thr Arg Lys Thr Ile
        115                 120                 125

Ser Gln Leu Phe Ala Lys Asn Lys Glu Ser Gln Arg Glu Lys Glu Lys
    130                 135                 140

Leu Glu Ala Glu Leu Ala Thr Ala Arg Ser Thr Asn Glu Asp Gln Arg
145                 150                 155                 160

Arg His Ile Glu Ile Arg Asp Gln Ala Leu Ser Asn Ala Gln Ala Lys
                165                 170                 175

Val Val Lys Leu Glu Glu Glu Leu Lys Lys Lys Gln Val Tyr Val Asp
            180                 185                 190

Lys Val Glu Lys Met Gln Gln Ala Leu Val Gln Leu Gln Ala Ala Cys
        195                 200                 205

Glu Lys Arg Glu Gln Leu Glu His Arg Leu Arg Thr Arg Leu Glu Arg
    210                 215                 220

Glu Leu Glu Ser Leu Arg Ile Gln Gln Arg Gln Gly Asn Cys Gln Pro
225                 230                 235                 240

Thr Asn Val Ser Glu Tyr Asn Ala Ala Leu Met Glu Leu Leu Arg
                245                 250                 255

Glu Lys Glu Glu Arg Ile Leu Ala Leu Glu Ala Asp Met Thr Lys Trp
            260                 265                 270

Glu Gln Lys Tyr Leu Glu Glu Asn Val Met Arg His Phe Ala Leu Asp
        275                 280                 285

Ala Ala Ala Thr Val Ala Ala Gln Arg Asp Thr Thr Val Ile Ser His
    290                 295                 300

Ser Pro Asn Thr Ser Tyr Asp Thr Ala Leu Glu Ala Arg Ile Gln Lys
305                 310                 315                 320

Glu Glu Glu Glu Ile Leu Met Ala Asn Lys Arg Cys Leu Asp Met Glu
                325                 330                 335

Gly Arg Ile Lys Thr Leu His Ala Gln Ile Ile Glu Lys Asp Ala Met
            340                 345                 350
```

```
             Ile Lys Val Leu Gln Gln Arg Ser Arg Lys Glu Pro Ser Lys Thr Glu
                     355                 360                 365

Gln Leu Ser Cys Met Arg Pro Ala Lys Ser Leu Met Ser Ile Ser Asn
                     370                 375                 380

Ala Gly Ser Gly Leu Leu Ser His Ser Ser Thr Leu Thr Gly Ser Pro
             385                 390                 395                 400

Ile Met Glu Glu Lys Arg Asp Asp Lys Ser Trp Lys Gly Ser Leu Gly
                             405                 410                 415

Ile Leu Leu Gly Gly Asp Tyr Arg Ala Glu Tyr Val Pro Ser Thr Pro
                         420                 425                 430

Ser Pro Val Pro Pro Ser Thr Pro Leu Leu Ser Ala His Ser Lys Thr
                     435                 440                 445

Gly Ser Arg Asp Cys Ser Thr Gln Thr Glu Arg Gly Thr Glu Ser Asn
                     450                 455                 460

Lys Thr Ala Ala Val Ala Pro Ile Ser Val Pro Ala Pro Val Ala Ala
             465                 470                 475                 480

Ala Ala Thr Ala Ala Ala Ile Thr Ala Thr Ala Ala Thr Ile Thr Thr
                             485                 490                 495

Thr Met Val Ala Ala Pro Val Ala Val Ala Ala Ala Ala Ala Ala Pro
                         500                 505                 510

Ala Ala Ala Ala Ala Pro Ser Pro Ala Thr Ala Ala Thr Ala Ala Ala
                     515                 520                 525

Ala Val Ser Pro Ala Ala Ala Gly Gln Ile Pro Ala Ala Ala Ser Val
                     530                 535                 540

Ala Ser Ala Ala Ala Val Ala Pro Ser Ala Ala Ala Ala Ala Ala Val
             545                 550                 555                 560

Gln Val Ala Pro Ala Ala Pro Ala Pro Val Pro Ala Pro Ala Leu Val
                             565                 570                 575

Pro Val Pro Ala Pro Ala Ala Gln Ala Ser Ala Pro Ala Gln Thr
                         580                 585                 590

Gln Ala Pro Thr Ser Ala Pro Ala Val Ala Pro Thr Pro Ala Pro Thr
                     595                 600                 605

Pro Thr Pro Ala Val Ala Gln Ala Glu Val Pro Ala Ser Pro Ala Thr
                     610                 615                 620

Gly Pro Gly Pro His Arg Leu Ser Ile Pro Ser Leu Thr Cys Asn Pro
             625                 630                 635                 640

Asp Lys Thr Asp Gly Pro Val Phe His Ser Asn Thr Leu Glu Arg Lys
                             645                 650                 655

Thr Pro Ile Gln Ile Leu Gly Gln Pro Asp Ala Glu Met Val Glu
                         660                 665                 670

Tyr Leu Ile
                     675

<210> SEQ ID NO 3
<211> LENGTH: 675
<212> TYPE: PRT
<213> ORGANISM: Homo sapiens
<220> FEATURE:
<221> NAME/KEY: VARIANT
<222> LOCATION: ()..()
<223> OTHER INFORMATION: Residue 135 = Asn, Ser or Asp
<220> FEATURE:
<221> NAME/KEY: VARIANT
<222> LOCATION: ()..(150)
<223> OTHER INFORMATION: Residues 148-150 = Glu-Leu-Ala or Thr-Thr-Pro
```

-continued

```
<400> SEQUENCE: 3

Met Pro Arg Ala Gln Pro Ser Ser Ala Ser Tyr Gln Pro Val Pro Ala
 1               5                  10                  15

Asp Pro Phe Ala Ile Val Ser Arg Ala Gln Gln Met Val Glu Ile Leu
             20                  25                  30

Ser Asp Glu Asn Arg Asn Leu Arg Gln Glu Leu Glu Gly Cys Tyr Glu
         35                  40                  45

Lys Val Ala Arg Leu Gln Lys Val Glu Thr Glu Ile Gln Arg Val Ser
     50                  55                  60

Glu Ala Tyr Glu Asn Leu Val Lys Ser Ser Lys Arg Glu Ala Leu
 65                  70                  75                  80

Glu Lys Ala Met Arg Asn Lys Leu Glu Gly Glu Ile Arg Arg Met His
                 85                  90                  95

Asp Phe Asn Arg Asp Leu Arg Glu Arg Leu Glu Thr Ala Asn Lys Gln
                100                 105                 110

Leu Ala Glu Lys Glu Tyr Glu Gly Ser Glu Asp Thr Arg Lys Thr Ile
            115                 120                 125

Ser Gln Leu Phe Ala Lys Xaa Lys Glu Ser Gln Arg Glu Lys Glu Lys
        130                 135                 140

Leu Glu Ala Xaa Xaa Xaa Thr Ala Arg Ser Thr Asn Glu Asp Gln Arg
145                 150                 155                 160

Arg His Ile Glu Ile Arg Asp Gln Ala Leu Ser Asn Ala Gln Ala Lys
                165                 170                 175

Val Val Lys Leu Glu Glu Glu Leu Lys Lys Lys Gln Val Tyr Val Asp
            180                 185                 190

Lys Val Glu Lys Met Gln Gln Ala Leu Val Gln Leu Gln Ala Ala Cys
        195                 200                 205

Glu Lys Arg Glu Gln Leu Glu His Arg Leu Arg Thr Arg Leu Glu Arg
    210                 215                 220

Glu Leu Glu Ser Leu Arg Ile Gln Gln Arg Gln Gly Asn Cys Gln Pro
225                 230                 235                 240

Thr Asn Val Ser Glu Tyr Asn Ala Ala Leu Met Glu Leu Leu Arg
                245                 250                 255

Glu Lys Glu Glu Arg Ile Leu Ala Leu Glu Ala Asp Met Thr Lys Trp
            260                 265                 270

Glu Gln Lys Tyr Leu Glu Glu Asn Val Met Arg His Phe Ala Leu Asp
        275                 280                 285

Ala Ala Ala Thr Val Ala Ala Gln Arg Asp Thr Thr Val Ile Ser His
    290                 295                 300

Ser Pro Asn Thr Ser Tyr Asp Thr Ala Leu Glu Ala Arg Ile Gln Lys
305                 310                 315                 320

Glu Glu Glu Glu Ile Leu Met Ala Asn Lys Arg Cys Leu Asp Met Glu
                325                 330                 335

Gly Arg Ile Lys Thr Leu His Ala Gln Ile Ile Glu Lys Asp Ala Met
            340                 345                 350

Ile Lys Val Leu Gln Gln Arg Ser Arg Lys Glu Pro Ser Lys Thr Glu
        355                 360                 365

Gln Leu Ser Cys Met Arg Pro Ala Lys Ser Leu Met Ser Ile Ser Asn
    370                 375                 380

Ala Gly Ser Gly Leu Leu Ser His Ser Ser Thr Leu Thr Gly Ser Pro
385                 390                 395                 400

Ile Met Glu Glu Lys Arg Asp Asp Lys Ser Trp Lys Gly Ser Leu Gly
                405                 410                 415
```

```
Ile Leu Leu Gly Gly Asp Tyr Arg Ala Glu Tyr Val Pro Ser Thr Pro
                420                 425                 430
Ser Pro Val Pro Pro Ser Thr Pro Leu Leu Ser Ala His Ser Lys Thr
            435                 440                 445
Gly Ser Arg Asp Cys Ser Thr Gln Thr Glu Arg Gly Thr Glu Ser Asn
    450                 455                 460
Lys Thr Ala Ala Val Ala Pro Ile Ser Val Pro Ala Pro Val Ala Ala
465                 470                 475                 480
Ala Ala Thr Ala Ala Ala Ile Thr Ala Thr Ala Ala Thr Ile Thr Thr
                485                 490                 495
Thr Met Val Ala Ala Pro Val Ala Val Ala Ala Ala Ala Ala Ala Pro
                500                 505                 510
Ala Ala Ala Ala Ala Pro Ser Pro Ala Thr Ala Ala Ala Thr Ala Ala
                515                 520                 525
Ala Val Ser Pro Ala Ala Gly Gln Ile Pro Ala Ala Ala Ser Val
                530                 535                 540
Ala Ser Ala Ala Ala Val Ala Pro Ser Ala Ala Ala Ala Ala Ala Val
545                 550                 555                 560
Gln Val Ala Pro Ala Ala Pro Ala Pro Val Pro Ala Pro Ala Leu Val
                565                 570                 575
Pro Val Pro Ala Pro Ala Ala Gln Ala Ser Ala Pro Ala Gln Thr
                580                 585                 590
Gln Ala Pro Thr Ser Ala Pro Ala Val Ala Pro Thr Pro Ala Pro Thr
                595                 600                 605
Pro Thr Pro Ala Val Ala Gln Ala Glu Val Pro Ala Ser Pro Ala Thr
                610                 615                 620
Gly Pro Gly Pro His Arg Leu Ser Ile Pro Ser Leu Thr Cys Asn Pro
625                 630                 635                 640
Asp Lys Thr Asp Gly Pro Val Phe His Ser Asn Thr Leu Glu Arg Lys
                645                 650                 655
Thr Pro Ile Gln Ile Leu Gly Gln Glu Pro Asp Ala Glu Met Val Glu
                660                 665                 670
Tyr Leu Ile
        675

<210> SEQ ID NO 4
<211> LENGTH: 143
<212> TYPE: PRT
<213> ORGANISM: Homo sapiens

<400> SEQUENCE: 4

Glu Ser Asn Lys Thr Ala Ala Val Ala Pro Ile Ser Val Pro Ala Pro
1               5                   10                  15
Val Ala Ala Ala Ala Thr Ala Ala Ala Ile Thr Ala Thr Ala Ala Thr
                20                  25                  30
Ile Thr Thr Thr Met Val Ala Ala Pro Val Ala Val Ala Ala Ala Ala
            35                  40                  45
Ala Ala Pro Ala Ala Ala Ala Pro Ser Pro Ala Thr Ala Ala Ala
    50                  55                  60
Thr Ala Ala Ala Val Ser Pro Ala Ala Gly Gln Ile Pro Ala Ala
65                  70                  75                  80
Ala Ser Val Ala Ser Ala Ala Ala Val Ala Pro Ser Ala Ala Ala Ala
                85                  90                  95
Ala Ala Val Gln Val Ala Pro Ala Ala Pro Ala Pro Val Pro Ala Pro
                100                 105                 110
```

-continued

```
Ala Leu Val Pro Val Pro Ala Pro Ala Ala Ala Gln Ala Ser Ala Pro
        115                 120                 125

Ala Gln Thr Gln Ala Pro Thr Ser Ala Pro Ala Val Ala Pro Thr
    130                 135                 140

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence:
      oligonucleotide primer for PCR reaction

<400> SEQUENCE: 5
tacggatccg aatcgaacaa aactgcagct g                              31

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence:
      oligonucleotide primer for PCR reaction

<400> SEQUENCE: 6
atactcgagt catggagctg gagttggagc ca                             32

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence:
      oligonucleotide primer for PCR reaction

<400> SEQUENCE: 7
gtttgacctg caatccagac aa                                        22

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer for PCR reaction

<400> SEQUENCE: 8
cccaggatct gaatgggagt t                                         21

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence:
      oligonucleotide primer for PCR reaction

<400> SEQUENCE: 9
cagatgggcc tgtgttccac tccaa                                     25

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:
      oligonucleotide primer for RACE PCR reaction
```

```
<400> SEQUENCE: 10
gctgacagtt gccctgacgc tgct                                              24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence:
      oligonucleotide primer for RACE PCR reaction

<400> SEQUENCE: 11
cggagacggt gctctagctg ctca                                              24

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence:
      oligonucleotide primer for RACE PCR reaction

<400> SEQUENCE: 12
tccttccaac tcttgcctca agttccg                                           27

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence:
      oligonucleotide primer for RACE PCR reaction

<400> SEQUENCE: 13
ggtggcagcg gacaggcagg atac                                              24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence:
      oligonucleotide primer for RACE PCR reaction

<400> SEQUENCE: 14
gaggcggaga gaactaagag aaga                                              24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence:
      oligonucleotide primer for RACE PCR reaction

<400> SEQUENCE: 15
gagcggagat ggaggagtaa ttca                                              24
```